(12) United States Patent
Cosner

(10) Patent No.: US 6,528,707 B1
(45) Date of Patent: Mar. 4, 2003

(54) IMPATIENS PLANTS AND METHODS OF REPRODUCTION

(75) Inventor: Harlan B. Cosner, Broadbent, OR (US)

(73) Assignees: Harlan Cosner, Rogue River, OR (US); Sue Cosner, Rogue River, OR (US)

( * ) Notice: Subject to any disclaimer, the term of this patent is extended or adjusted under 35 U.S.C. 154(b) by 0 days.

(21) Appl. No.: 09/468,483

(22) Filed: Dec. 16, 1999

Related U.S. Application Data

(63) Continuation-in-part of application No. 09/169,593, filed on Oct. 9, 1998.

(51) Int. Cl.⁷ ................................................. A01H 5/00
(52) U.S. Cl. ........................ 800/323; 800/260; 800/266
(58) Field of Search ................................ Plt./318, 319; 800/323, 260, 266

(56) References Cited

U.S. PATENT DOCUMENTS 5,684,225 A * 11/1997 Drewlow et al. ........... 800/200

OTHER PUBLICATIONS

Winters, Harold F., "Branched Pedicels in New Guinea Impatiens", Jun. 1982, HortScience vol. 17 (3):340–341.*

* cited by examiner

*Primary Examiner*—Bruce R. Campell
*Assistant Examiner*—Susan B. McCormick
(74) *Attorney, Agent, or Firm*—Ganz Law, PC; Bradley M. Ganz, Esq.

(57) ABSTRACT

A new and distinctive New Guinea Impatiens plant characterized by flowers with two or more colors distributed in irregular randomly distributed patterns on some or all petals and flower. The patterns are defined by multiple irregularly shaped regions of color. Generally, each region consists of an elongate streak or patch of color typically radiating in a direction from the base of a petal to the edge of the petal. The irregularly shaped regions, while not necessarily exclusive of other colors, generally are dominated by a single color. The streaks or patches forming regions may vary in color intensity, shape, length, and width. They may also vary in terms of their position relative to the base and edge of a petal. The novel features of the invention also include a method of producing multiple sports from crosses of the present invention with other novel plants of the present invention or with conventional New Guinea Impatiens plants. The invention further relates to novel New Guinea impatiens that have two or more pedicels per peduncle. And, it relates to both single and double New Guinea impatiens plants with the foregoing characteristics.

35 Claims, 12 Drawing Sheets

(8 of 12 Drawing Sheet(s) Filed in Color)

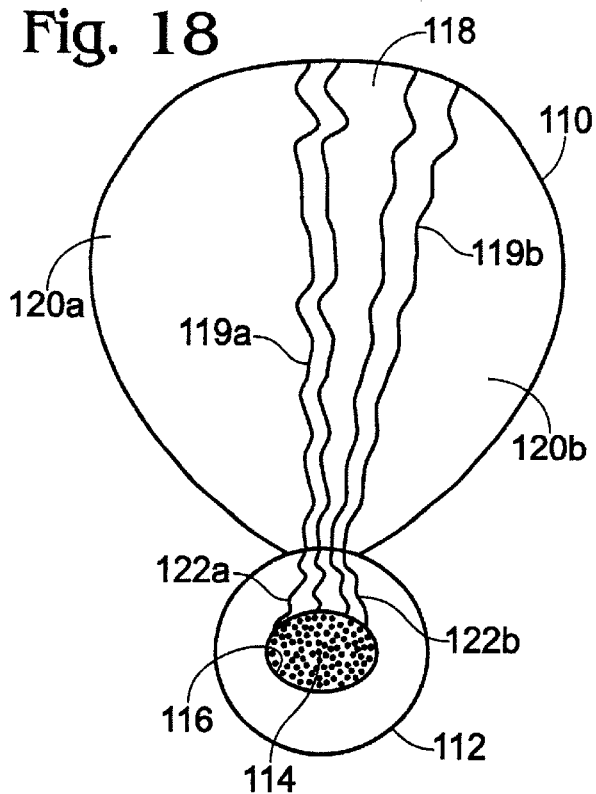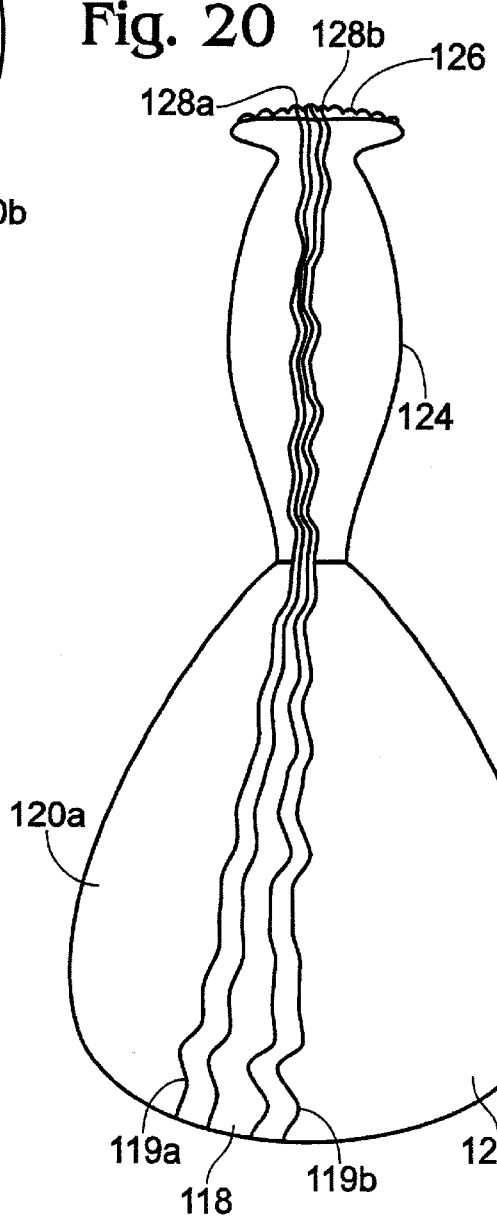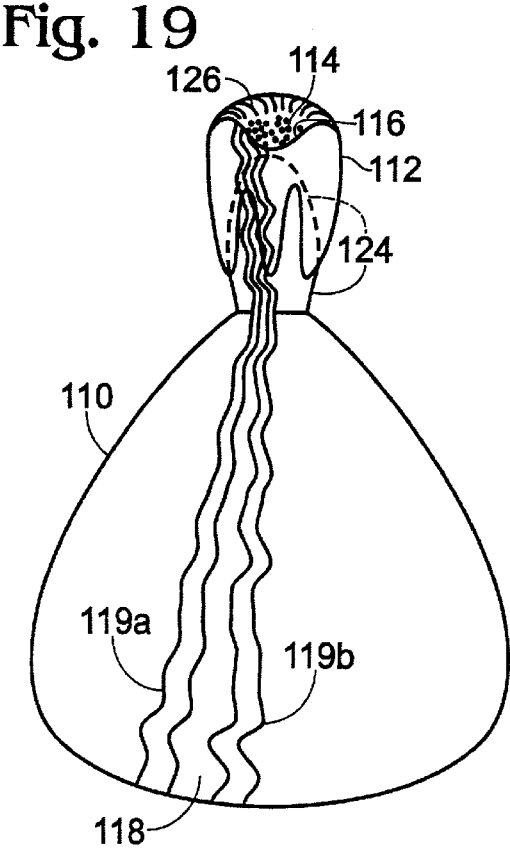

IMPATIENS PLANTS AND METHODS OF REPRODUCTION

BACKGROUND OF THE INVENTION

This application is a continuation-in-part of pending Serial No. 09/169,593 filed on Oct. 9, 1998 entitled "Novel Impatiens Plants and Methods for Reproduction".

The present invention relates to novel varieties of New Guinea impatiens plants, botanically known as Impatiens Hawkeri, and methods for reproducing the same. More particularly the invention relates to New Guinea impatiens plants having a flower with a novel, random, multi-colored pattern. The invention also relates to novel New Guinea impatiens plants that produce multiple sports off a single seedling. The invention further relates to novel New Guinea impatiens plants that have multiple flowers off multiple pedicles of a single peduncle.

Impatiens plants are one of the most popular garden plants due to their versatility. Sales of impatiens varieties are currently estimated at 250 million dollars per year. They are favorites for beds, borders, pots and hanging baskets. Impatiens require relatively little maintenance. And they have a relatively long blooming season, generally ranging through summer and fall. When impatiens plants drop their faded flowers, new flowers come to replace the ones dropped. This is not the case for other flowering plants such as Geraniums.

Impatiens are available as single or double flowering plants. But not all single flowering varieties are available as doubles. Generally the double flowering varieties are sterile and do not produce seeds. Because of this, double flower forms are propagated asexually.

The three commercially significant species of impatiens are hawkeri, more commonly known as "New Guinea", walleriana, and balsamina. The hawkeri species does not cross with the walleriana species. Nor is it believed to cross with balsamina. Although walleriana impatiens plants generally are more stable and vigorous than New Guinea impatiens, walleriana flowers are smaller and less bright than New Guinea impatiens flowers. In addition to having larger, brighter flowers, New Guinea plants are larger and hold their petals longer. Because the New Guinea varieties do not interbreed with the walleriana varieties, it is not possible through normal breeding practices to transfer desirable flower characteristics and other genetic characteristics between hawkeri and walleriana varieties. For example, there is one variety of walleriana with flowers speckled with two or more color patterns marketed by Ball Seed Company of West Chicago, Ill., for example, under the names Mosaic Lilac and Mosaic Rose. See Ball Seed Company Catalog, 1998–99, p.31. Such a variety is not known in the New Guinea impatiens species.

The lucrative market for impatiens plants is not content with existing varieties of New Guinea impatiens. New Guinea impatiens plants were introduced for commercialization only relatively recently, in about 1972. See D. A. Bailey, *Commercial Production of New Guinea Impatiens*, Horticulture Leaflet 526, rev'd 4/95-Author Reviewed 4/97, North Carolina Cooperative Extension Service, North Carolina State University. Accordingly, there is still substantial demand for additional aesthetic varieties. Gardeners are continually looking for a wider range of aesthetic options to stand alone or complement other aspects of their gardens. Unfortunately, existing varieties of New Guinea impatiens have not been well developed due to the species relatively recent commercial introduction. Consequently, among other things, they offer relatively little choice beyond solid color flowers and bicolor flowers in a relatively small range of fixed color patterns.

The flower coloration of currently available commercial New Guinea impatiens cultivars encompasses three basic configurations. These are solid colored flowers without an eye, as in Electra Hot White, U.S. Pat. No. 10259 to Cosner; solid colors with an eye of another color, as in Electra Royale, U.S. Pat. No. 10,300 to Cosner; and star patterns, as in Lasting Impressions Ambiance, U.S. Pat. No. 8903, assigned to Oglevee Ltd.

Referring to FIG. 1 of this specification, four examples of the conventional New Guinea impatiens flower types are shown, along with a novel flower according to the present invention (center flower). The flower on the far left is a conventional solid colored flower named "Jolana" with a slightly pronounced eye. To the immediate right of Jolana, is a conventional solid colored flower named "Electra Royale" with a more pronounced eye. As mentioned, the center flower to the right of Electra Royale is one example of a novel flower of the present invention that is named "ElRed". This flower is shown to demonstrate some novel features of the present invention relative to the conventional varieties shown. This novel flower and others are described in more detail below. To the immediate right of ElRed is a conventional bright-eye type flower named "Woya" with a pronounced eye. The flower on the far right, next to Woya, is a conventional star type flower named "Ambiance". Each of the foregoing conventional flowers is commercially available from different distributors.

Plant breeders face a persisting challenge of producing a series of a plant that can be potted or bedded together to create a grouping of plants that look is and grow the same but which can produce a variety of flower effects. This creates a desirable and commercially-important aesthetic effect. The challenge in achieving such an effect persists because plants with different flower colors and patterns normally are produced by plants with different genetic backgrounds. While it may be possible to select plants with different genetic backgrounds that appear to have similar growth habits in a controlled green house environment, the growth habits of the plants may be quite different when introduced into the environment provided by the end user. The differences may cause the potted or bedded plants to vary in size, shape, flowering time etc., creating unacceptable aesthetic effects. Accordingly there is a need for breeding stock that can produce different flower colors and patterns but which grow and resemble each other in all other respects.

In practice, to overcome the drawbacks of using plants with different genetic backgrounds to form a series, breeders have looked for plants showing two more sports (hereinafter "multiple sports"). In the context of this discussion, a sport is a portion of a plant having different colors or color patterns than the color and color patterns of other flowers on the same plant. Plants producing two or more sports are commercially advantageous because plants propagated from each sport type will have the identical growth habits. Each sport type may be asexually reproduced and sold together as a series.

X-rays or chemical mutagens have been typically used to induce multiple sports off a single seedling. This process is unpredictable and has a low yield. Moreover, it is expensive, inconvenient, and inherently dangerous to use x-ray labs or chemical mutagens to induce the sports. A simpler, less expensive, safer, and more predictable process of producing asexually reproducible sports off a single seedling would be desirable and advantageous.

Conventional New Guinea impatiens plants also suffer the drawback of blossoming only a single flower per peduncle. Some New Guinea impatiens cultivars may have two or peduncles fused at their bases. Examples of such plants include the commercial varieties Celebration "Purple Star", Ball Flora Plant, West Chicago, Ill. and "Bonaire" (U.S. Pat. No. 9137) Paul Ecke Ranch, Encinitas, Calif. The flowers produced from fused peduncles suffer the problem of holding the flowers too tightly to the foliage, making the inflorescence less dramatic. In some non-New Guinea plant species the inflorescence is more dramatic because the peduncle produces multiple pedicels, each of which produces a single flower held above the foliage by the pedicels. For example, the walleriana impatiens species has varieties that produce multiple pedicels from a single peduncle. The flowers of the plant are held above the foliage. A plant with two pedicels per peduncle doubles the number of flowers per plant. A plant with three pedicels per peduncle has triple the number of flowers per plant. Plant varieties with multiple pedicels are desirable because the increased number of flowers per plant creates a more dramatic inflorescence. This makes varieties with multiple flower producing pedicels commercially advantageous. Unfortunately, New Guinea impatiens plants with multiple pedicels have not yet is been successfully bred for commercialization.

SUMMARY OF THE INVENTION

The present invention provides stable aesthetically exciting new varieties of New Guinea impatiens plants that overcome the aforementioned disadvantages of the prior art. The novel plants display flowers with a blend of two or more colors in irregularly shaped random patterns, creating a "tie-dye" or marbled effect. One of the most apparent advantages of the present invention is an always-changing color pattern wherever it is used—whether it is in hanging baskets, other types of containers, or in ground beds—the always-changing color pattern of the novel tie-dye impatiens makes the landscape come alive.

Its uniqueness will complement virtually all other New Guinea impatiens cultivars without the colors clashing. When these novel plants are crossed with themselves or other New Guinea impatiens plants, including conventional and other tie-dye plants, some seedlings have flowers with the tie-dye effect, and other seedlings have conventional flowers. When the plants having conventional flowers are reproduced sexually, seedlings with a relatively high frequency of sports are produced. The different branches may then be asexually reproduced to create a series of plants that produce flowers of different colors or patterns but which have identical growth habits.

The present invention also provides novel New Guinea impatiens that have multiple pedicels, which increases the flower count per plant, making the plants more lively and colorful.

The present invention can be expressed in terms of various embodiments reflecting distinct new varieties of New Guinea impatiens plant. In a most basic embodiment, the variety is of a New Guinea impatiens plant having at least one flower characterized by a marbling effect in at least two or more petals of the flower, said plant being asexually reproducible into other plants showing at least one flower with a similar marbling effect.

The present invention also contemplates a plant having at least one flower with at least three petals with the marbling effect. The present invention further contemplates a plant wherein about 30% or more of the flowers in the plant have some petals with the marbling effect.

The present invention also contemplates a plant wherein predominantly all flowers of the plant have some petals with the marbling effect.

The present invention also contemplates a plant wherein predominantly all flowers of the plant have predominantly all petals with the marbling effect.

The present invention also contemplates a plant wherein at least one flower has predominantly all petals with a marbling effect of three or more colors.

The present invention also contemplates a plant wherein about 30% or more of the flowers in the plant have some petals with a marbling effect of three or more colors.

The present invention also contemplates a plant that includes at least two sports.

The present invention also contemplates a plant that includes at least three sports.

The present invention also contemplates a method of producing a New Guinea impatiens plant comprising:

(a) crossing a New Guinea impatiens plant cultivar having marbling in its background with a different or same New Guinea Impatiens plant cultivar having marbling in its background;

(b) selecting progeny that show some degree of marbling in at least one flower petal; and (c) repeating steps (a) to (b) until a plant is produced having at least one flower characterized by a marbling effect in at least two or more petals of the flower, said plant being asexually reproducible into other plants showing at least one flower with a similar marbling effect.

The present invention also contemplates that in this method, steps (a) to (b) may be repeated until the produced plant has a flower with at least three petals with a marbling effect.

The present invention also contemplates that in the method, the steps may be repeated until predominantly all petals in at least one flower of the produced plant have the marbling effect.

The present invention also contemplates that in the method, the steps may be repeated until about 30% or more of the flowers in the produced plant have some petals with the marbling effect.

The present invention also contemplates that in the method, the steps may be repeated until predominantly all flowers of the produced plant have the marbling effect.

The present invention also contemplates that in the method, the steps may be repeated until the marbling effect is of three or more colors.

The present invention further contemplates that in the method, the steps may be repeated until a plant is produced wherein predominantly all flowers have predominantly all petals with the marbling effect.

The present invention also contemplates a method wherein a selected plant may be backcrossed to a parent.

The present invention also contemplates a method wherein the plant selected in step (b) has a higher degree of marbling than either parent plant.

The present invention also contemplates a method wherein during any initial or repeat cross of step (a), the initial plant or selected plant from step (b) may have at least one flower with predominantly all petals with the marbling effect.

The present invention also contemplates a method wherein at least one of the plants crossed in step (a) may have about 30% or more of its flowers with predominantly all petals having a marbling effect.

The present invention also contemplates a method wherein at least one of the plants crossed in step (a) may have predominantly all flowers with predominantly all petals having a marbling effect.

The present invention also contemplates a method wherein both plants crossed in step (a) may each have about 30% or more flowers with predominantly all petals having a marbling effect.

The present invention also contemplates a method wherein a selected plant may be backcrossed to itself.

The present invention also contemplates a method wherein a selected plant may be backcrossed to other selected plants.

The present invention also contemplates a method wherein one of the plants having marbling in its background used in the initial cross of step (a) may have two or more flowers with predominantly all petals displaying marbling.

The present invention also contemplates a method for producing a New Guinea impatiens plant comprising:
- selecting a first New Guinea impatiens plant cultivar having a predetermined degree of marbling, the first plant being asexually reproducible into other plants having a similar degree of marbling;
- selecting a second predetermined New Guinea Impatiens plant cultivar;
- crossing the first and second plants;
- selecting progeny that show a suitable degree of marbling;
- repeating the steps as necessary to produce a plant with a desired degree of marbling; and
- asexually propagating progeny showing the desired characteristic.

The present invention also contemplates that in the preceding method, one of the New Guinea impatiens plant cultivars for the cross may have two or more flowers with at least two or more petals having marbling.

The present invention also contemplates that in the method, the second New Guinea impatiens plant may comprise a plant having flowers predominantly all of which are of a conventional type.

The present invention also contemplates that in the method, the second plant may have flowers predominantly all of which have a marbling effect.

The present invention also contemplates that in the method, both of the New Guinea impatiens plants for the cross may have predominantly all flowers with the marbling effect.

The present invention also contemplates a method, for producing a New Guinea impatiens plant that has multiple sports comprising:
- selecting a first New Guinea impatiens plant cultivar having a predetermined degree of marbling, the first plant being asexually reproducible into other plants having a similar degree of marbling;
- selecting a second predetermined New Guinea Impatiens plant cultivar;
- crossing the first and second plants;
- selecting progeny that show at least two sports;
- repeating the steps as necessary to produce a plant with at least two sports; and
- asexually propagating one or more sports from a selected plant.

The present invention also contemplates that in the preceding method, the progeny showing at least three sports per plant may be selected and asexually propagated.

The present invention also contemplates that in the method for producing multiple sports, progeny showing at least four sports per plant may be selected for asexual propagation.

The present invention also contemplates that in the method for producing multiple sports, at least one of the plants crossed may have about 30% or more of its flowers with predominantly all petals displaying a marbling effect.

The present invention also contemplates that in the method for producing multiple sports, at least one of the plants crossed in step (a) may have about 30% or more of its flowers with predominantly all petals displaying a conventional flower type.

The present invention also contemplates that in the method for producing multiple sports, the second plant may comprise a plant having flowers predominantly all of which are of a conventional flower type.

The present invention also contemplates that in the method for producing multiple sports, the first plant may comprise a plant having flowers predominantly all of which have a marbling effect.

The present invention also contemplates a New Guinea impatiens plant having at least two flowerable pedicels arising from at least one peduncle on at least one branch of the plant, said plant being asexually reproducible into a plant having about the same degree of pediceling.

The present invention also contemplates a plant wherein at least one peduncle has at least three pedicels.

The present invention also contemplates a plant wherein at least one branch on the plant has at least two peduncles, each giving rise to multiple pedicels.

The present invention also contemplates a plant wherein at least two branches on the plant each have at least one peduncle giving rise to multiple pedicels.

The present invention also contemplates a plant with multiple pedicels wherein the plant includes a predetermined degree of marbling in its background.

The present invention also contemplates a plant wherein two or more branches on the plant each have at least one peduncle giving rise to multiple pedicels.

The present invention also contemplates a plant wherein two or more branches on the plant further include two or more peduncles on a single branch, each giving rise to multiple peduncles.

The present invention also contemplates a method of producing a New Guinea impatiens plant comprising:
(a) crossing a New Guinea impatiens plant having multiple pediceling in its background with a different or same New Guinea impatiens plant having multiple pediceling in its background;
(b) selecting progeny that show some degree of multiple pediceling in at least one or more peduncles on a branch; and
(c) repeating steps (a) to (b) as necessary until a plant is produced having at least two flowerable pedicels arising from at least one peduncle on at least one branch of the plant, said plant being asexually reproducible into another plant having about the same degree of pediceling as its parent.

The present invention also contemplates that in the method of producing a plant with multiple pediceling, steps (a) to (b) may be repeated as necessary until the produced plant has at least one peduncle with at least three pedicels.

The present invention also contemplates that in the method of producing a plant with multiple pediceling, steps (a) to (b) may be repeated as necessary until the produced plant has at least one branch with at least two peduncles each giving rise to multiple pedicels.

The present invention also contemplates that in the method of producing a plant with multiple pediceling, the steps may be repeated as necessary until at least two branches on the plant each have at least one peduncle giving rise to multiple pedicels.

The present invention also contemplates that in the method of producing a plant with multiple pediceling, at least one of the parents in the initial cross may have marbling in its background.

The present invention also contemplates that in the method of producing a plant with multiple pediceling, the plant selected in step (b) may have a higher degree of pediceling than either parent plant.

The present invention also contemplates that in the method of producing a plant with multiple pediceling, during any initial or repeat cross of step (a), the initial plant or selected plant from step (b) may produce about 30% or more of its flowers with a marbling effect.

The present invention also contemplates that in the method of producing a plant with multiple pediceling, a selected plant may be backcrossed to itself in one or more crosses of the method.

The present invention also contemplates that in the method of producing a plant with multiple pediceling, a selected plant may be backcrossed to other selected plants in one or more crosses of the method.

The present invention also contemplates that in the method of producing a plant with multiple pediceling, a selected plant may be backcrossed to one of its parents in one or more crosses of the method.

The present invention also contemplates that in the method of producing a plant with multiple pediceling, the steps may be repeated until about 30% or more of the branches in the produced plant each have at least one peduncle with multiple flowerable pedicels.

The present invention also contemplates a novel New Guinea impatiens plant having at least two branches each with at least one peduncle, said plant having marbling in its background, said plant being asexually reproducible into is other plants showing at least two branches each having at least one peduncle with multiple pedicels.

The present invention also contemplates a plant having multiple pediceling with at least two sports.

The present invention also contemplates a plant having multiple pediceling with at least three sports.

The present invention also contemplates a plant having multiple pediceling wherein the plant displays flowers predominantly, all of which are of a conventional type.

The present invention also contemplates a plant having multiple pediceling wherein the plant displays flowers predominantly, all of which have marbling.

The present invention also contemplates a double New Guinea impatiens plant having marbling, multiple pediceling and/or multiple sports of the same degree as single New Guinea impatiens plants.

The present invention also contemplates a method of producing a novel New Guinea impatiens wherein a plant with a predetermined degree of multiple pediceling, and which is asexually reproducible into other plants with about the same degree of pediceling, is crossed with a plant not having multiple pediceling to produce progeny having multiple pediceling and desired characteristics of the plant without multiple pediceling.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2b is an example of another novel marbled flower according to the present invention, similar to FIG. 2a.

FIG. 18 is a top view illustrating certain reproductive structures of a New Guinea impatiens plant.

FIG. 19 is a side partial sectional view illustrating certain reproductive structures of a New Guinea impatiens plant.

FIG. 20 is a side view illustrating certain reproductive structures of a New Guinea impatiens plant.

DETAILED DESCRIPTION OF THE INVENTION

For purposes of this specification, references to flower "color" may mean distinct colors or distinct shades of the same color. The Royal Horticultural Society Colour Chart rating codes are used for rating colors, unless ordinary dictionary terms are used. Unless indicated otherwise, the term "plant" as used herein means a variety of New Guinea impatiens plant.

Figure 1:
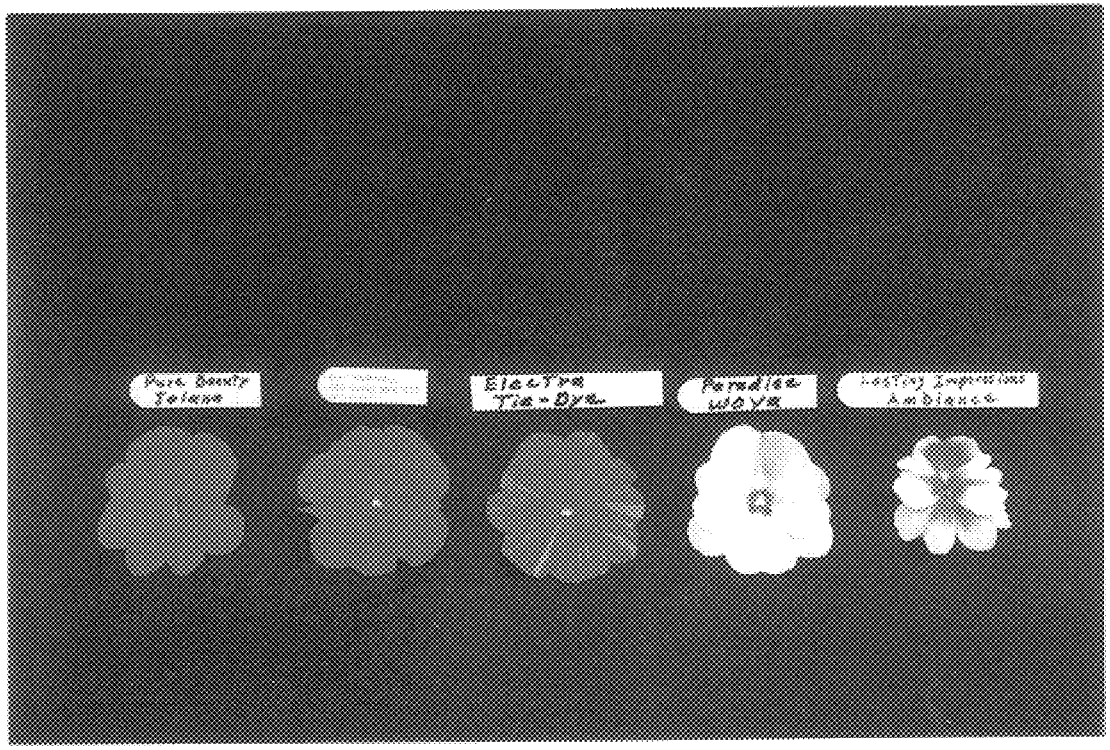
FIG. 1 comparatively shows a novel marbled flower according to the present invention that is in the center of the photograph, and two different conventional flowers to the left of the novel flower, and two different conventional flowers to the right of the novel marbled flower.
Figure 2A:
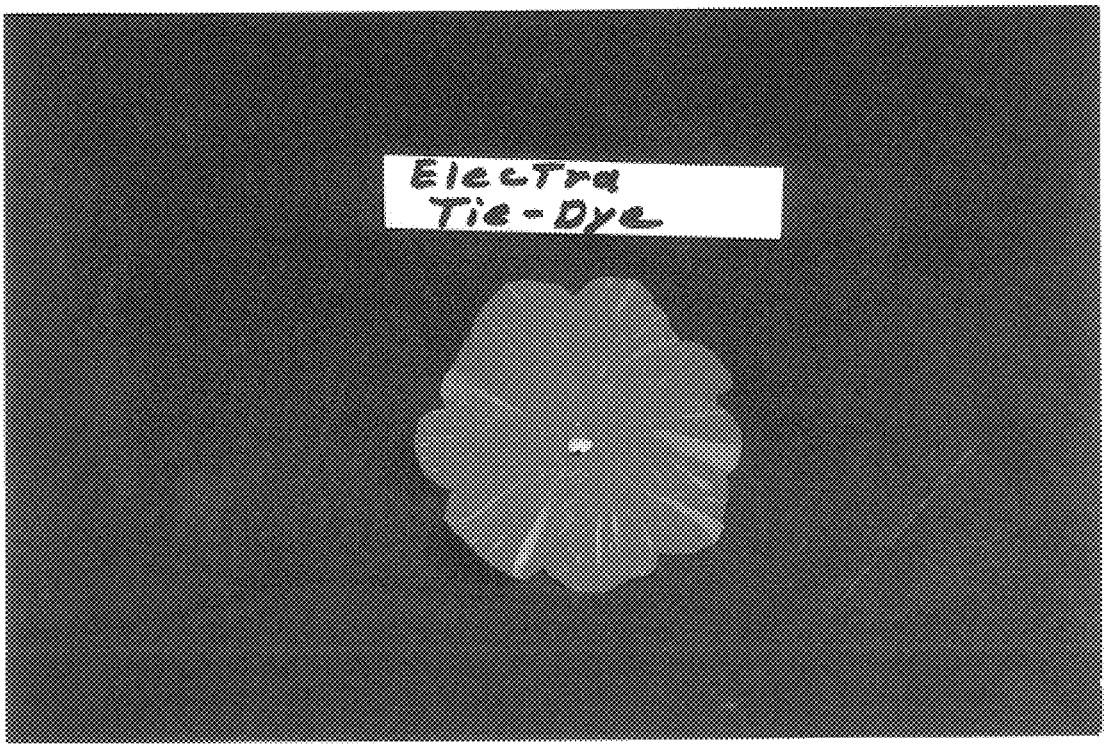
FIG. 2a shows a photo of the novel marbled flower in the center of FIG. 1 without the other flowers in FIG. 1.
Figure 2B:
Figure 3:
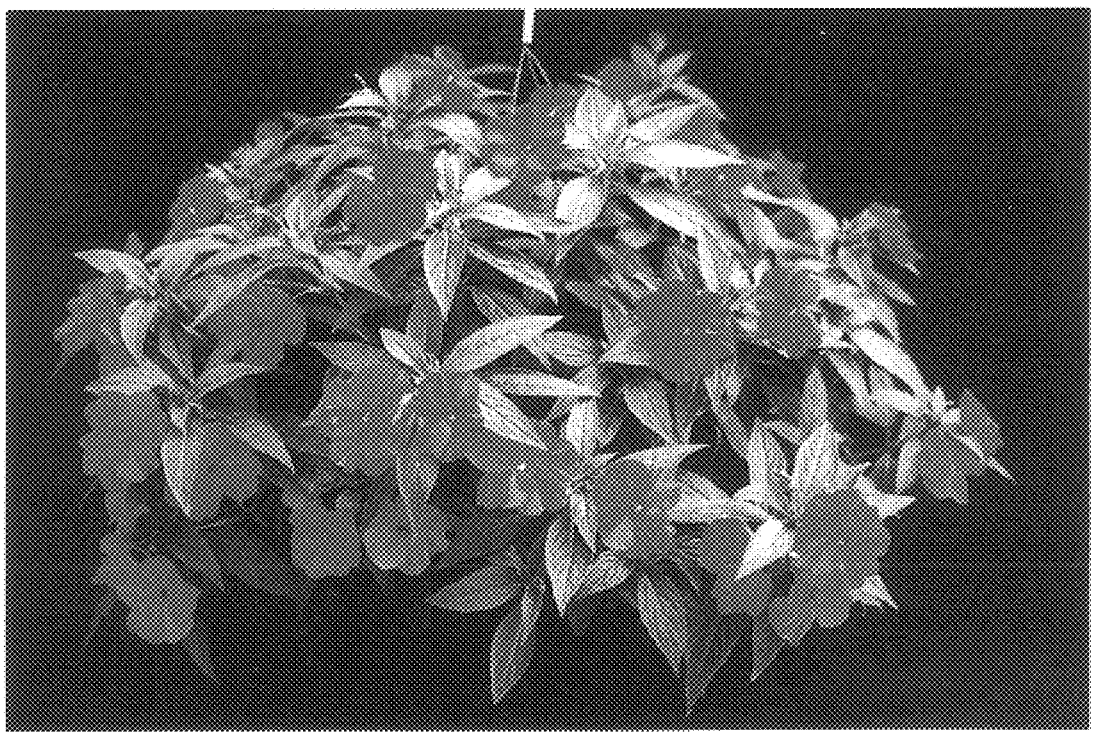
FIG. 3 shows three flowering New Guinea impatiens plants according to the present invention, one or more of which were the sources of the flowers shown in FIGS. 2a and 2b.
Figure 4:
FIG. 4 shows a portion of a New Guinea impatiens plant according to the present invention with flowers similar to the flowers of FIG. 2, the plant also having multiple sports.

FIGS. 2–4 show New Guinea impatiens flowers, and plants having marbled flowers, according to the present invention. FIGS. 2a and 2b show different flowers produced by a plant according to the present invention. Relative to multi-color flowers of the prior art, which have predictable and regular color patterns, such as the Star or Bright Eye varieties of FIG. 1, the colors on flowers of the present invention, examples of which are shown in FIGS. 2–4, are distributed in distinctive irregular, randomly distributed patterns on some or all petals of some or all flowers. The patterns are defined by multiple irregularly shaped regions of color. Generally, each region consists of an elongate streak or patch of color typically radiating in a direction from the base of a petal to the edge of the petal. The irregularly shaped regions, while not necessarily exclusive of other colors, generally are dominated by a single color. The streaks or patches forming regions may vary in shape, length, width, and color intensity. They also may vary in terms of their position relative to the base and edge of a petal. As used herein, the terms "marbled", "marbling" and variations of these words shall refer to a petal or flower having patterns as described in this paragraph.

FIG. 3 shows a 10" container with three individual plants with flowers showing the marbling effect. One of the plants shown in FIG. 3 produced the flowers shown in FIG. 2. Each of these plants has flowers similar to the flowers of FIG. 2. As is typical for New Guinea varieties, the plants shown in FIG. 3 produce about 15–25 flowers open at a time per plant. Each peduncle on the plants shown in FIG. 3 produces only one flower. In FIG. 3, all flowers and petals of each plant show the marbling effect. The degree of marbling varies from petal to petal.

A typical flower shown in FIGS. 2–3 has random markings on the adaxial of 51A, 50A, 61B and 71B with a darker mark at the base of the petals of 60A. The abaxial surface of the top petal has the typical center ridge, which is close to 187B. The remainder of this petal and the other four petals have random markings close to 61C, 63A, and 43C. Top of buds prior to opening are 187B.

FIG. 4 shows another New Guinea impatiens plant with three flowers according to the present invention. The marbling effect occurs in the two flowers in the foreground of the photo. The rearward flower displays a conventional flower type of solid color with a pronounced eye. Accordingly, this plant displays multiple sports, another novel feature of the present invention, which is described below in more detail.

The two marbled flowers of FIG. 4, and the plant producing them, are generally similar to those shown in FIGS. 2–3, except the marbled flowers of FIG. 4 have different colors. The other flowers from the plant producing the marbled flowers are not marbled. Rather they have solid colors of orange to light salmon, with a dark eye. The adaxial surface of the marbled flowers of FIG. 4 has a reddish purple spot at the base of each petal, the remainder is marbled with 49A and 33A. The abaxial surface of the marbled flowers in FIG. 4 is 49A and 33A, with a typical center ridge being colored close to 58C. As can be seen, the colors are distributed in the same way as the flowers of FIGS. 2–3, namely in random, irregularly shaped patterns.

The colors and color patterns of the foregoing figures are illustrative, and the present invention is not limited to the flower colors shown in the accompanying figures. Nor the particularly patterns shown. Other color combinations, color distributions, and random patterns on petals and flowers are expected to result by practicing the teachings of this invention.

To breed plants that produce flowers with the novel marbling effect of the present invention, a novel breeding method is used. Starting with a population of conventional plants, a plant is selected that shows marbling in its genetic background.

A plant showing some degree of stable or unstable marbling, including a plant with flower petals with unstable, off-color stripe or spotting, shown in FIG. 5 discussed below, and plants with the marbled flowers of FIGS. 2–4, and any other plant with this genotype, is hereinafter referred to as having "marbling in its genetic background." New Guinea impatiens plants with varying degrees of marbling effects are now available from Tioga Genetics, Broadbent Oreg., which company is owned and operated by the inventor named herein.

A single petal showing a random stripe or off color spotting in a single petal is observed to be the most basic phenotypic expression of a plant having marbling in its background. Examples of petals of such flowers are shown in FIG. 5. The detached flower petals in the lower left, center, and right of FIG. 5 were found as single petals on different flowers of different conventional New Guinea impatiens plants known as Pascua and Prepona. These varieties are marketed through, Paul Ecke, Ranch, Encinitas, Calif. (The initial plants used to produce the plants of FIGS. 2–4 are from a different; unknown source and no longer are available to be photographed.) In FIG. 5, the two detached petals on the bottom left side of the photograph are examples of ones with a slight degree of off-colored spotting or marbling. The detached petal on the far right is an example of a petal with an off-color striping or marbling. Arrows in the photos point to the off-colored areas in the petals. The flower above the detached petal on the left shows the normal color pattern of the plant variety from which the petal below comes. The flower above the detached petal on the right shows the same for the petal below.

The off-coloring characteristics seen in these examples of conventional flowers is unstable; it is not reproduced through asexual reproduction of the flowering portion of the plant showing the characteristic. This unstable characteristic is an infrequent, but observable phenotype, which, in the inventor's experience of having observed many thousands of New Guinea impatiens, has not been seen to occur in more than a single petal of a flower at a time.

A plant producing marbled flowers that can asexually be reproduced may be created according to a novel method of this invention. A plant having marbling in its background is crossed with itself or a different plant having marbling in its background using well known techniques. A suitable technique is manual transfer of viable pollen from the anther of one plant to a receptive stigma in the other plant. If different plants are used in the cross, the flowers can have the same or different colors.

The resulting F1 seedlings are grown out, and plants having flower petals showing marbling are selected for asexual reproduction or further crosses in the same manner.

The resulting F1 plants may be evaluated to determine whether the degree of marbling in the F1 is stable. If the degree of marbling is stable, the plants may be asexually reproduced for commercial sale, or for use as breeding stock. Even if the trait has not been stabilized, the plants may be used in further crosses, as described below.

In this early stage, if plants showing the unstable off-color stripe or spotting were used as the parents, the patterns and colors on the petals of the F1 seedlings, and other early generations, are not likely to be as distinctive as the fully developed patterns of the flowers shown in FIGS. 2–4. Rather, such F1 seedlings are more likely to have a degree of marbling like that in the parent plant, as represented by the petals of FIGS. 5. These petals may be considered to have a low degree of marbling. Generally, as described below, further crosses will be necessary to produce plants with a higher degree of marbling.

As used herein, a higher degree of marbling is characterized by more distinct marbling patterns on a petal, more petals per plant with marbling, more flowers per plant with marbling, and so forth. The plants shown in FIGS. 2–4 have a relatively high degree of marbling because marbling is present in each flower of the plant, and all petals of each flower, to varying degrees, as shown.

As a general rule, plants with higher degrees of marbling may be bred, and the number of crosses necessary to produce plants with higher degrees of marbling may be minimized, by choosing as parents for successive crosses the progeny from earlier crosses that show the highest degree of marbling. For example, it has been observed that when starting with parents of the unstable plant that produces a petal of the type shown in FIG. 5, each succeeding generation shows an increased tendency of the resulting plants to have more petals per flower and more flowers per plant with marbling. In addition, the patterns become more distinctive with each generation, transitioning from the colors and patterns shown in FIG. 5 to the colors and patterns shown in FIGS. 2–4, for example.

To produce succeeding generations of a plant with marbling, an F1 seedling, or later generation seedling or plant, showing a desired pattern may be backcrossed with (1) its parent that shows marbling; (2) crossed with itself;(3) crossed to other seedlings or plants in the same or different generation that show marbling; (4) crossed with other related or unrelated plants showing marbling; or (5) crossed with unrelated or related plants not showing marbling.

At any generation where the plant has marbling effects that are aesthetically desirable, cuttings may be taken to determine whether the plant may be asexually propagated for commercial production, breeding, seed production, or other desired purposes. If starting with parents of the unstable plant that produces a petal of a type shown in FIG. 5, after about 3–5 generations of successive crosses as described above, a stable, asexually reproducible seedling will result that has predominantly all petals of predominantly all flowers with the marbling effect, as represented by the flowers and plants of FIGS. 2–4. If starting with an already stable plant with marbling, fewer crosses may be necessary to produce new stable varieties of marbled plants. However, depending on the flower characteristics actually desired, and the genetic variables at work, a higher or lower number of crosses may be needed for any particular breeding attempt.

This invention contemplates still other new varieties of New Guinea impatiens plants with marbling in their background that may result using the methods of this invention. The new varieties may include plants with marbled flowers having different color combinations and effects. Such plants are expected to result from successive crosses of marbled flowers with conventional plants having a desired color or combinations of colors. Plants showing marbling in the desired colors are selected for further crosses until the desired result is achieved.

For purposes of this invention, a New Guinea impatiens plant that produces enough flowers to create an overall visual impression of marbling in the plant as a whole shall be considered as having "predominantly all flowers with the marbling effect. A plant with at about $3/4^{ths}$ (75%) of its flowers with the marbling effect should create this impression even if remaining flowers do not have marbling. Similarly, a flower that produces enough petals with the marbling effect to create an overall visual impression of marbling in the flower as a whole shall be considered as having "predominantly all petals with the marbling effect. A plant with at least about $3/5^{ths}$ (60%) of its flowers with the marbling effect should create this impression even if remaining petals do not have marbling.

Seedlings with desired characteristics may be selected for asexual reproduction. As used herein, asexual reproduction means multiplying the plant without the use of genetic seeds to produce a true copy of the plant being reproduced, particularly with regard to a selected characteristic. Regarding the present invention, an asexually reproducible plant is one that shows about the same degree of marbling or other selected characteristic present in the parent plant. Such plants may also be referred to as "stable". In the present invention, stable marbled plants produce progeny with the same color combinations as the parent, and to about the same degree, although the color may be arranged in different irregularly shaped patterns on the flowers, and not necessarily in the same relative amounts.

Any known (or to be developed) method of asexual reproduction applicable to New Guinea impatiens may be used in the present invention including, for example: root cuttings, apomictic seeds, division, layering, tissue culture, grafting and budding, slips, nuclear embryos, or other known means of copying the genetic material to reproduce plants expressing the desired marbling characteristics.

The methods of this invention may further involve crossing to produce other novel plants, as described below.

1. Stable, Novel Marbled New Guinea Impatiens× Conventional New Guinea Impatiens A cross of a stable, marbled New Guinea impatiens, of a type shown in FIGS. 2–4, with a conventional New Guinea Impatiens will produce seedlings of both parents'phenotypes. Initial studies suggest that the phenotype of the conventional type dominates. The observed ratio is about ¾ (75%) conventional and about ¼ (25%) marbled.

2. Stable, Novel Marbled New Guinea Impatiens×Stable, Novel Marbled New Guinea Impatiens Crosses between the same or different stable marbled plants of this invention produce seedlings with (1) marbled flowers and (2) plants with the conventional phenotypes such as the solid, Star or Bright Eye patterns. Initial studies suggest that the phenotype of the conventional cultivar predominates. The observed ratio is also about ¾ (75%) conventional and about ¼ (25%) marbled.

It has been surprisingly found that among the seedlings resulting from the crosses of (1) stable marbled plant to conventional plants and (2) stable marbled plants to stable marbled plants are a relatively high percentage of plants with multiple sports. It has been observed that about one in fifty (1/50) seedlings of such crosses produce plants having two or more asexually reproducible sports. In contrast, in conventional populations of New Guinea impatiens, a plant producing a single sport is extremely rare. In the inventor's experience such sports appear no more frequently than at least about one in every six thousand (1/6000) seedlings, absent x-rays or chemical mutagens.

As used herein a "sport" refers to a first portion of a plant capable of producing a single flower type in terms of colors and/or patterns, the first portion of the plant being asexually reproducible into other plants producing the same flower type, the plant having one or more other portions producing a different flower type that may be asexually reproduced into other plants with such different flower type(s). Where a plant has such differing flower types, any portion producing such flower type may be referred to as a sport. By this definition, the minimum number of sports a plant may have is two. The plants asexually reproduced from sports have identical or similar growth habits and flowering times. While different plants asexually reproduced from different sports of a plant will have identical or similar growth habits and flowering times, the plants possibly may have variations in foliage colors.

Figure 6:
FIG. 6 shows a novel New Guinea impatiens plant according to the present invention with two different sports in the background that each have a flower with a star pattern, and a third sport in the foreground with a novel marbled flower, with marbling being present in each petal of the flower.

In terms of the present invention, the number of sports has been observed to vary from two to about three per plant. FIGS. 4 and 6 show examples of plants producing multiple sports. In the case of FIG. 6, the plant shown has three sports. The two sports in the background have star patterns, and the sport in the foreground has a marbled effect in all petals. The three sports shown in FIG. 6 were asexually reproducible into stable cultivars with identical growth habits and flowering times. Accordingly, plants that show two or more sports may be selected and asexually propagated for use in a series.

In more detail, the marbled flower in the foreground FIG. 6 has petals marbled with 74A, 41A, 41D, 49D, 64B, 59B in the top (adaxial) surface and a top center petal with the foregoing colors and additional colors of 42A and 61B in the top surface. The white sport in the background of FIG. 6 has a flower with a base spot of 53D, and dark stripe of 55A. The rest of the petals are a purple, white of 76D. The purple sport, also in the background of the marbled sport, has a flower with a top surface with a dark spot of 62A on the center petal, a dark stripe of 71D on each of the other petals, and a base spot of 57A on each petal with the rest of the petal being close to 74C or 74d. The purple and white sports are asexually reproducible and are stable. The marbled sport also appears stable. Except for flower colors, all three sports asexually reproduced into plants that have all the same general characteristics in terms of flower time, habit, and growth when they were grown in the same place and under the same cultural practices.

Figure 7:
FIG. 7 shows a portion of a novel New Guinea impatiens plant according to the present invention with two fully developed, twin ovaries attached to a single peduncle of a branch.
Figure 8:
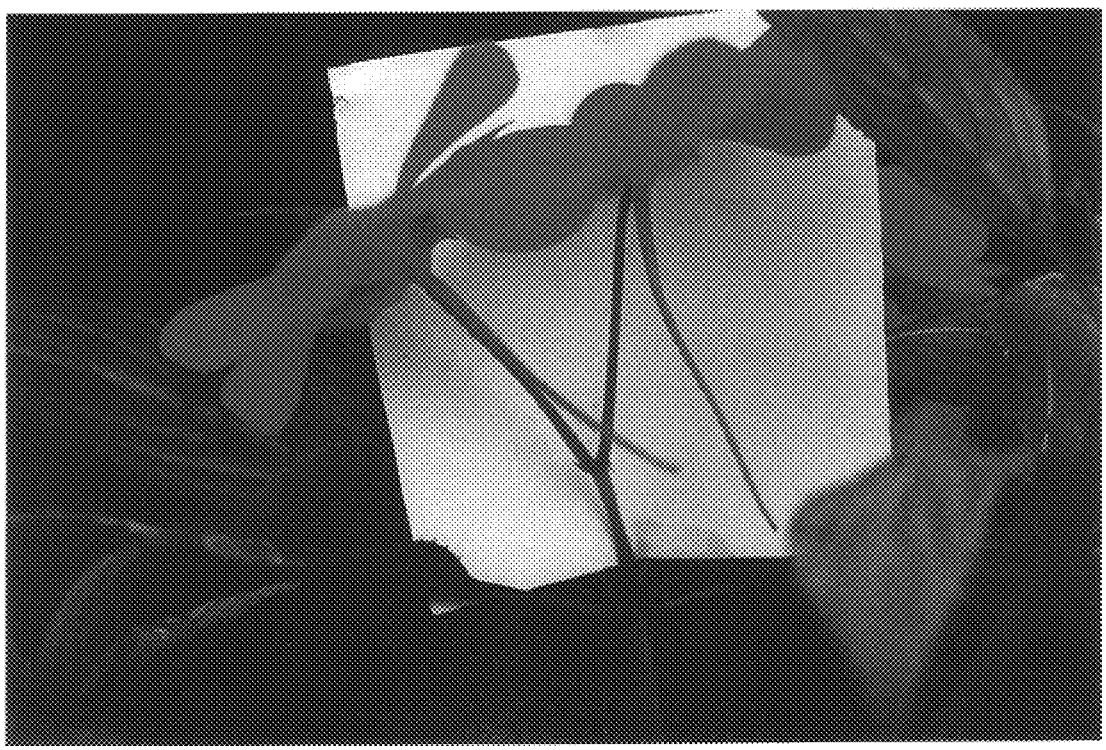
FIG. 8 shows a portion of a novel New Guinea impatiens plant according to the present invention with two flowers, each arising from a separate pedicel on a single peduncle.
Figure 9:
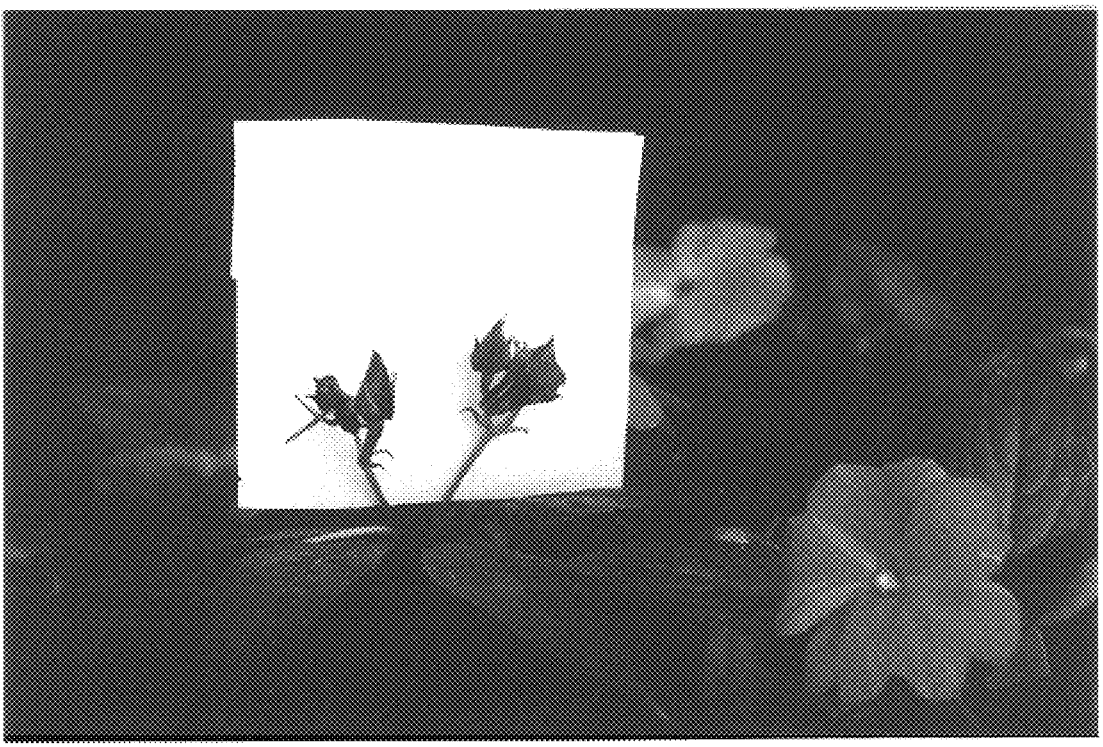
FIG. 9 shows a portion of a novel New Guinea impatiens plant with multiple peduncles on a single branch, each peduncle with multiple pedicels, each pedicel producing a flower, some of the plants flowers displaying a marbling effect.

The inventor has created further novel plants by crossing: (1) plants with marbling in their background with conventional plants; or (2) plants with marbling in their background with plants with marbling in their background. These crosses produced a low, but regularly observable percentage of seedlings that have branches with a single peduncle, each peduncle with multiple ovaries. FIG. 7 shows a portion of a New Guinea impatiens plant with two fully developed, twin ovaries attached to a single peduncle of a branch. It can be seen that the peduncle appears somewhat like two peduncles fused together. In this case, the pedicels have not yet developed from the peduncle. But further breeding results in a single, normal appearing peduncle giving rise to two developed pedicels, each having a flower-producing ovary. The ovaries are each located at the end of a pedicel, rather than directly at the end of a peduncle. For example, FIG. 8 shows a New Guinea impatiens plant with two solid color flowers, each arising from separate pedicels. Each of those two pedicels arises from the same peduncle on a branch. This example was produced from further crosses of the plant shown in FIG. 7 with itself or other flowers having multiple pediceling in their background. FIG. 9 shows the seed parent of the plant of FIG. 8.

The plant of FIG. 9 shows a novel New Guinea impatiens plant with multiple peduncles on a single branch, each branch with multiple pedicels and each producing a flower. Some of the flowers are a marbled type. Other branches from the same plant, not shown in FIG. 9, also had multiple peduncles on a branch, each with multiple pedicels, each producing a normal flower of a conventional or marbled type. Although not shown in FIG. 9, this plant also produced peduncles fused at their bases, like seen in Celebration Purple Star discussed in the background section. The individual peduncles in the fused unit either directly produced a single flower or produced multiple pedicels each with a flower of the marbled type. Accordingly, fused peduncles producing multiple pedicels are another novel aspect of the invention. The plant of FIG. 9 also produced multiple sports of conventional and marbled flower types. The plant shown in FIG. 9 is the asexual progeny of an earlier plant with the same characteristics. Those characteristics include multiple branches with multiple peduncles each having multiple pedicels, each of which produces a conventional or marbled flower. Clones of the plant of FIG. 9 also showed the same characteristics.

The plants of the present invention that have two or more pedicels per peduncle on one or more branches may be of the conventional or marbled phenotype. Such plants are of great significance to the breeding of New Guinea impatiens because there has yet to be a stable New Guinea impatiens plant that could be stably reproduced with multiple pedicels. These plants may be used to produce further New Guinea impatiens plant varieties with higher degree of multiple pediceling. Thus, the present invention makes it possible to produce a higher degree of inflorescence relative to existing varieties of single and double New Guinea impatiens plants.

To create breeding or commercial stock of plants with multiple pediceling, a plant having marbling in its background is crossed with itself or a different plant with or without marbling in its background. Again, a suitable technique is manual transfer of viable pollen from the anther of one plant to a receptive stigma in the other plant using a known technique. If different plants are used in the cross, the flowers can have the same or different colors and/or patterns.

The resulting F1 seedlings are grown out, and plants, such as the one shown in FIG. 7, having one or more peduncles, each showing a tendency for producing two or more ovaries or pedicels are selected for asexual reproduction or further crosses in the same manner. Any plant having the genotype for, or showing a phenotypical tendency for, multiple ovaries or pedicels per a single peduncle is hereinafter referred to as "having multiple pediceling", or "pediceling" for shorthand, in its background." An example of a plant with a low degree of multiple pediceling is shown in FIG. 7. Examples of plants with relatively higher degrees of multiple pediceling include those shown in FIGS. 8–9.

The resulting F1 plants may be evaluated to determine whether the degree of pediceling in the F1 is stable. If the degree of pediceling is stable, the plants may be asexually reproduced for commercial sale, for use as breeding stock, or seed production. Even if the trait has not been stabilized, the plants may be used for breeding in further crosses, as described below. It should be noted that plants having multiple pediceling may produce flowers of the conventional type or flowers of the marbled type.

In early crosses using a plant with a twined peduncle, like the one shown in, FIG. 7, it has been observed that about 10% or less of the progeny from such crosses will show multiple pediceling. Generally, as described below, further crosses will be necessary to produce plants with higher degrees of multiple pediceling. To produce plants with higher degrees of pediceling, and to minimize the number of crosses necessary to reach a desired degree of pediceling, plants showing relatively higher degrees of pediceling should be selected for use in successive, subsequent crosses, as a general rule.

To produce such succeeding generations, an F1 seedling, or later generation seedling, showing a desired degree of multiple pediceling may be backcrossed with (1) its parent that has multiple pediceling in its background; (2) crossed with itself; (3) crossed to other seedlings in the same or different generation that have multiple pediceling in their back-ground; (4) crossed with other related or unrelated plants showing multiple pediceling; or (5) crossed with a plant without multiple pediceling in its background.

At any generation where the plant has a desired degree of multiple pediceling, cuttings may be taken to determine whether the plant may be asexually propagated for commercial production, breeding stock, seed production, or other desired purpose.

Starting with a plant showing some multiple pediceling in its background, which is selected from parents having a high degree of marbling in their background, after about at least four generations of crosses, as described above, a stable, asexually reproducible seedling should result that has at least about 30% of its branches, each with at least one peduncle having multiple pedicels, capable of producing normal flowers. However, depending on the flower characteristics actually desired, and the genetic variables at work, a higher or lower number of crosses may be needed for any particular breeding attempt.

For purposes of this invention, a New Guinea impatiens plant that produces enough flowers to create an overall visual impression of each branch having at least one peduncle giving rise to multiple pedicels, shall be considered as having "predominantly all branches with multiple pediceling". A plant with about $\frac{3}{4}^{ths}$ (75%) of its branch having a peduncle with multiple pedicels should create this impression even if the remaining branches do not have multiple pedicels on a branch.

Seedlings with desired characteristics may be selected for asexual reproduction. Any known (or to be developed) method of asexual reproduction applicable to New Guinea impatiens may be used including, for example: root cuttings, apomictic seeds, division, layering, tissue culture, grafting and budding, slips, nuclear embryos, or other known means of copying the genetic material to reproduce plants expressing the desired multiple pedicel characteristics.

Figure 14:
FIG. 14 shows a portion of a New Guinea impatiens plant with multiple pediceling, each pedicel with multiple flowers, according to the present invention.
Figure 15:
FIG. 15 shows a second view of the portion of the plant from FIG. 14, the plant portion having multiple peduncles with multiple pedicels.
Figure 16:
FIG. 16 shows a third view of the portion of the plant from FIG. 15.

FIG. 14 shows a branch portion of a New Guinea impatiens plant with multiple pediceling. The plant is identified as BP-22 under the inventor's breeding program. BP-22 was produced from a cross of a clone off S-286C (pollen parent) and BP-8 (seed parent). S-286C was a clone selected from K-286 for its stable marbling characteristics. BP-8 was a seedling from a cross of S-286C (pollen parent) and BP-1 (seed parent) The S-286C variety, is available under the name "ElPur" from Paul Ecke Ranch, Encinitas, Calif., under license from the inventor of the present application. (Plant codes correspond to those in Table 2 below). Each peduncle has two or more flowers (or buds). Three of the peduncles can be seen to have three or more buds, each bud developed on a separate pedicel. The plant was produced using the breeding methods described above. FIG. 15 shows a second view of the same branch portion of the plant from FIG. 14. It can be seen that the plant produces multiple peduncles, each with multiple pedicels. One pedicel produces three flower buds, as seen in FIG. 15. FIG. 16 shows a third view of the same portion of the plant shown in FIG. 15, further illustrating the foregoing multiple pedicel characteristics. The plant produced at least 16 solid purple flowers per whorl. In contrast, conventional New Guinea impatiens plants produce 6–8 flowers per whorl. As a result of the multiple pediceling in the plant of FIGS. 14–16, the plant displayed an excellent inflorescence, yielding at least 30–50 or more flowers open at a time per plant. This is a substantial improvement over the typical 15–25 flowers open at a time for a conventional New Guinea impatiens plant.

The novel single New Guinea impatiens plants of this invention may be bred to produce double New Guinea impatiens using known techniques. For example, U.S. Pat. No. 5,684,225 for "Double Flowering New Guinea Impatiens" describes a method of producing double New Guinea impatiens plants. The '225 patent is hereby expressly incorporated by reference for its teachings on breeding and growing single and double impatiens plants. As elaborated above, by using plants with marbling in their background, novel plants having multiple, flower-producing pedicels on a single peduncle have been produced. It is expected that plants with doubleness in their background, as defined in the '225 patent, may be used in the method steps of the present invention, and as described in the '225 patent, to produce New Guinea impatiens plants displaying marbled, double flowers. These marbled, double plants may have at least one single double flower per peduncle. They may also have two or more flowers off multiple pedicels from a single peduncle. It is also expected that plants with marbling in their background may also be used in the method steps of the present invention, and as described in the '225 patent, to produce double New Guinea impatiens plants displaying multiple sports by one or more crosses of plants with a high degree of marbling with other plants having doubleness in their background.

Figure 10:
FIG. 10 shows a portion of a novel New Guinea impatiens plant according to the present invention with multiple pedicels and double flowers.

An example of a plant with multiple pediceling, double flowers, and marbling in its background, experimentally bred by the inventor, is shown in FIG. 10. This plant produces flowers of a double type with a conventional solid color. About 10% or less of the peduncles on the various branches each produce multiple pedicels, with each pedicel having a double flower within the terminology of the '225 patent. The flowers have a pronounced dark eye at the base of the petals, surrounded by a whitish ring, and the remainder of the petals are a solid red. In this plant, the petal count varies per flower, ranging from about 5–10. Each flower has normally shaped, double flowers. The plant shown in FIG. 10 is the first generation progeny of a cross of the plant shown in FIG. 9, which was the female, with a conventional double New Guinea impatiens plant, the male. The male plant had flowers of a light scarlet color. The male had doubling in its background within the terminology of the '225, but it did not have marbling in its background.

The following tables detail certain New Guinea impatiens plants according to the present invention. The tables are provided for example purposes only; it is believed the invention is adequately enabled by the foregoing disclosure. Table 1 is a key to the codes used in the subsequent tables. Column 1 gives a number corresponding to a color or pattern observed in the flowers from the plants listed in Table 2. Column 2 gives a number corresponding to the foliage color of the plants listed in Table 2. Column 3 gives a number corresponding to the general habit of the plants listed in Table 2. Column 4 gives a number corresponding to notable positive or negative characteristics of the plants listed in Table 2. (The numbers used in the Table 1 and 2 to indicate color are not based on the Royal Horticultural Society Colour Chart.)

TABLE 1

| FLOWER | FOLIAGE | HABIT | CHARACTERESTIC |
|---|---|---|---|
| 1. Red Purple | 1. Green | 1. Short | 1. Open |
| 2. Blue Purple | 2. Bronze | 2. Medium | 2. Well Branched |
| 3. Red-scarlet | 3. Dark Green | 3. Tall | 3. Small Leaves |
| 4. Pink | 4. Black Green | 4. Compact | 4. Large Leaves |
| 5. Lavender | 5. Brown Green | 5. Ideal | 5. Small Flower |
| 6. Salmon-coral | 6. Red Green | 6. Ideal | 6. Large Flower |
| 7. Fuchsia-cherry | 7. Bronze Green | 7. Tall | 7. Wilts Easy |
| 8. White | 8 | 8. Short | 8. Flowers in Cycles |
| 9. Red Bicolor | 9. | 9. Medium | 9. Flowers in Heat |
| 10. Orange | 10. Varigated | 10. | 10. Drought Tolerant |
| 11. Orange Bicolor | 11 | 11. Short | 11. Pineapples |
| 12. Bicolor | 12 | 12. Tall | 12. Cupped Flowers |
| 13. Star | 13 | 13. Medium | 13. Flat Flowers |
| 14. Picotee | 14 | 14. | 14. Semi-double |
| 15. Hot Pink/White | 15. Rolled Down | 15 | 15. Double |
| 16. Hot Pink/Deep rose | 16 | 16 | 16. Gappy Flowers |
| 17. Cherry Red | 17 | 17. Early | 17. Fades |
| 18. Purple Bicolor | 18 | 18. Medium | 18. Flowers Last |
| 19. Apple Blossom | 19. Wide | 19. Late | 19. Flowers in Foliage |
| 20. Blue Pink | 20. Flat | 20 | 20. Flowers above Foliage |
| 21. Salmon-Coral/White | 21. Narrow | 21 | 21. Long Peduncle |
| 22. | 22. Pointed | 22 | 22. Short Peduncle |
| 23. Some degree of stable marbling present in one or more petals | 23. Horizontal | 23 | 23. Multiple Flowers per Peduncle |
| 24. | 24. Upright | 24 | 24. Long Leaves |
| 25. | 25. Quilted | 25. Full | 25. Round Leaves |
| 26. | 26. Droopy | 26. Open | 26. Serrated Leaves |
| 27. | 27. Shiny | 27. | 27. Smooth Leaves |
| 28. | 28. Dull | 28. Upright | 28. Shiny Foliage |
| 29 | 29. Fuzz | 29. Spread | 29. Dull foliage |
| 30 | 30. Serrated | 30. Horizontal | 30. Fuzzy Foliage |
| 31 | 31. Thick | 31 | 31. Good Pollen Prod. |
| 32 | 32. Thin | 32 | 32. Poor Pollen Prod. |
| 33 | 33 | 33 | 33. Good Female |
| 34 | 34 | 34 | 34. Poor Female |
| 35 | 35. Rolled Up | 35 | 35. Flat Follage |
| 36 | 36 | 36 | 36. High Fl. Count |
| 37 | 37 | 37 | 37. Low Fl. Count |
| 38. Flat-poor | 38 | 38 | 38. Uneven |
| 39. Medium | 39 | 39 | 39. Wild-Ratty |
| 40. Good | 40 | 40 | 40. Uniform |
| 41. Excellent | 41 | 41 | 41. Discard |

In Table 2 below, Column 1 lists a plant identification code number assigned by the inventor. Column 2 identifies, respectively, the male and female parents of the plants listed in column 1. Columns 3–6 correspond to the characteristics coded under the same headings in Columns 1–4 of Table 1. Hyphens in Columns 2–6 link multiple applicable coding numbers. In all cases, the plants are New Guinea impatiens grown in the location and under the conditions described in the example below detailing the plant named "ElRed".

TABLE 2

| No. | MALE x FEMALE. | FLOWER | FOLIAGE | CHARACTERISTICS | HABIT |
|---|---|---|---|---|---|
| BR-10 | Unknown, occasional off color stripe in a single petal | 4-38 | 1 | 16-31-5-2-8 | 2-26 |
| HC-12 | Unknown, occasional off color stripe in a single petal | 5-38 | 3 | 16-31-5-2 | 2-30 |
| H-1 | BR-10 x HC-12 | 1-39 | 5 | 16-17-5-31 | 2-25 |
| K-18 | HC-12 x BR-10 | 4-39 | 2 | 16-18-5-33 | 2-25 |
| P-23 | HC-12 x BR-10 | 11-38 | 2 | 13-18-5-33 | 2-26 |
| F-24 | BR-10 x HC-12 | 6-38 | 3 | 16-18-6-33 | 2-25 |
| K-1 | F-24 x K-18 | 23/11-4-40 | 1 | 2-13-18-20-31-33 | 2-25 |
| P-160 | H-1 x P-23 | 6-39 | 3-25 | 2-16-32-34 | 2-25 |
| BR-279 | P-23 x F-24 | 5-40 | 3 | 2-4-13-32-34 | 2-26 |
| F-327 | K-18 x F-24 | 11-23, one | 10-25 | 1-16-19-32-33 | 2-26 |

TABLE 2-continued

| No. | MALE x FEMALE. | FLOWER | FOLIAGE | CHARACTERISTICS | HABIT |
|---|---|---|---|---|---|
| | | flower is 23/10-3 | | | |
| S-108 | P-160 x K-1 | 11 occasional striping of 6 | 2 | 13-20-31-34 | 1-26-29 |
| S-486 | K-1 x F-327 | 1 | 3 | 13-20-32-34 | 5-25 |
| S-486A | k-1 x F-327 Sport of S-486 | 1 w/ occasional striping of 5 | 3 | 13-20-32-34 | 5-25 |
| J-2095 | BR-279 x K-1 | 3-39 | 7 | 13-20-31-34 | 2-25 |
| S-486B | Sport of S-486A | 23/1-(2 or 5) (reverted to 486A after | 2 | 13-20-32-34 | 5-25 |
| A-2110 | S-486A x S-108 | 23/6-1 | 1 | 2-13-26-18-17-31-34 | 2/3-25 |
| K-3180A | K-1 x S-486B | 7 | 3 | 2-5-20-31-34 | |
| J-5397 | Reselection of J-2095 | 23 | | | |
| BP-1 | J-5397xK-286 | 17-more rose | | | |
| L-146 | Sport of A-2110 | 23/6-1 | 1 | 2-6-13-20-31-34 | 2-25 |
| ST-3417A | K-3180 x A-2110 | 1/4 (red purple or pink)-13 (star) of 3- occasional stripe of 5 | 4 | 2-6-13-20-31-34 | 2-25 |
| K-286 | S-486 x S-108 | 23-2/5 | 7 | 2-5-20-23-31-33 | 2/3-25 |
| SF-2 | ST-3417A x S-486 | | | | |
| L-146-3 | Reselection of L-146 | 23-1/6 | 1 | 2-6-13-20-31-34 | 2-25 |

Figure 5:
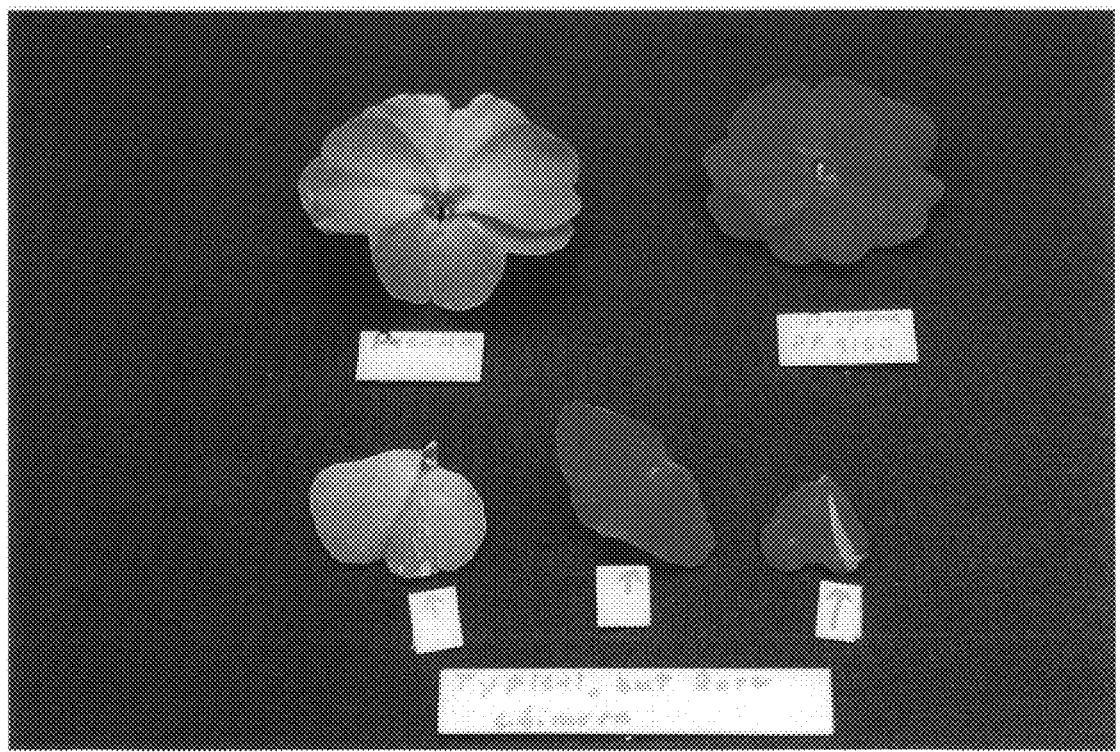
FIG. 5 show petals and flowers found in conventional New Guinea impatiens plant with an infrequent off-coloring that indicates a plant is suitable for use as a parent in a breeding method according to the present invention.

The plants identified above as BR-10 and HC-12 were selected as parents for the initial crosses because they showed an occasional petal with an off-color stripe, examples of which are shown in FIG. 5. Progeny from the crosses of BR-10 and HC-12 also showed an occasional off-color striping, although the specific progeny having this feature are not noted in the Table 2. Further crosses of such progeny produced plants where the off-color stripe appeared to be stabilizing and developing into a higher degree of marbling. One of these plants includes the plant identified as K-1. The pertinent crosses are further detailed in FIGS. 11–13.

Figure 11:
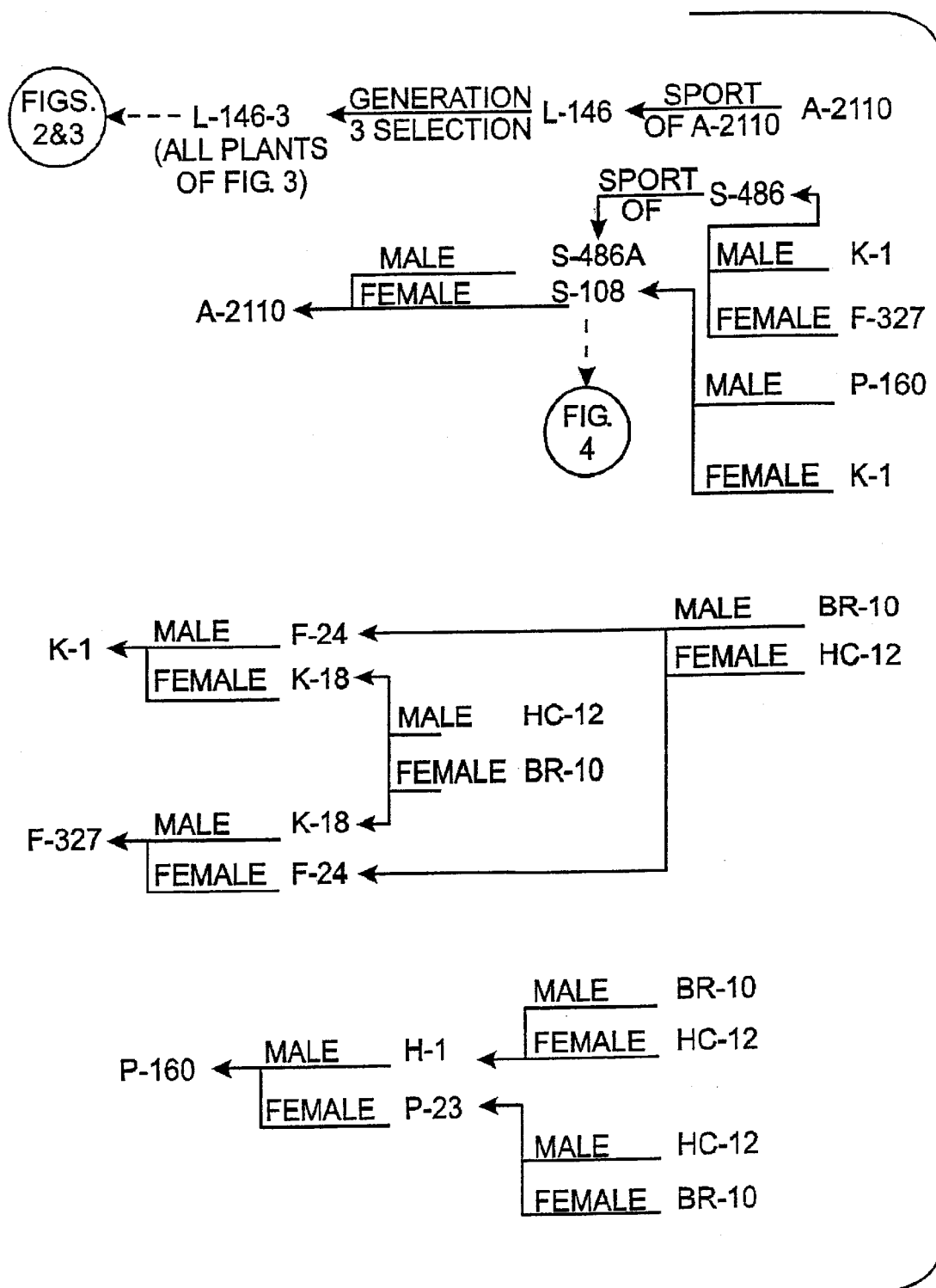
FIGS. 11–13 show the lineages of certain novel plants bred by novel methods according to the present invention.
Figure 12:
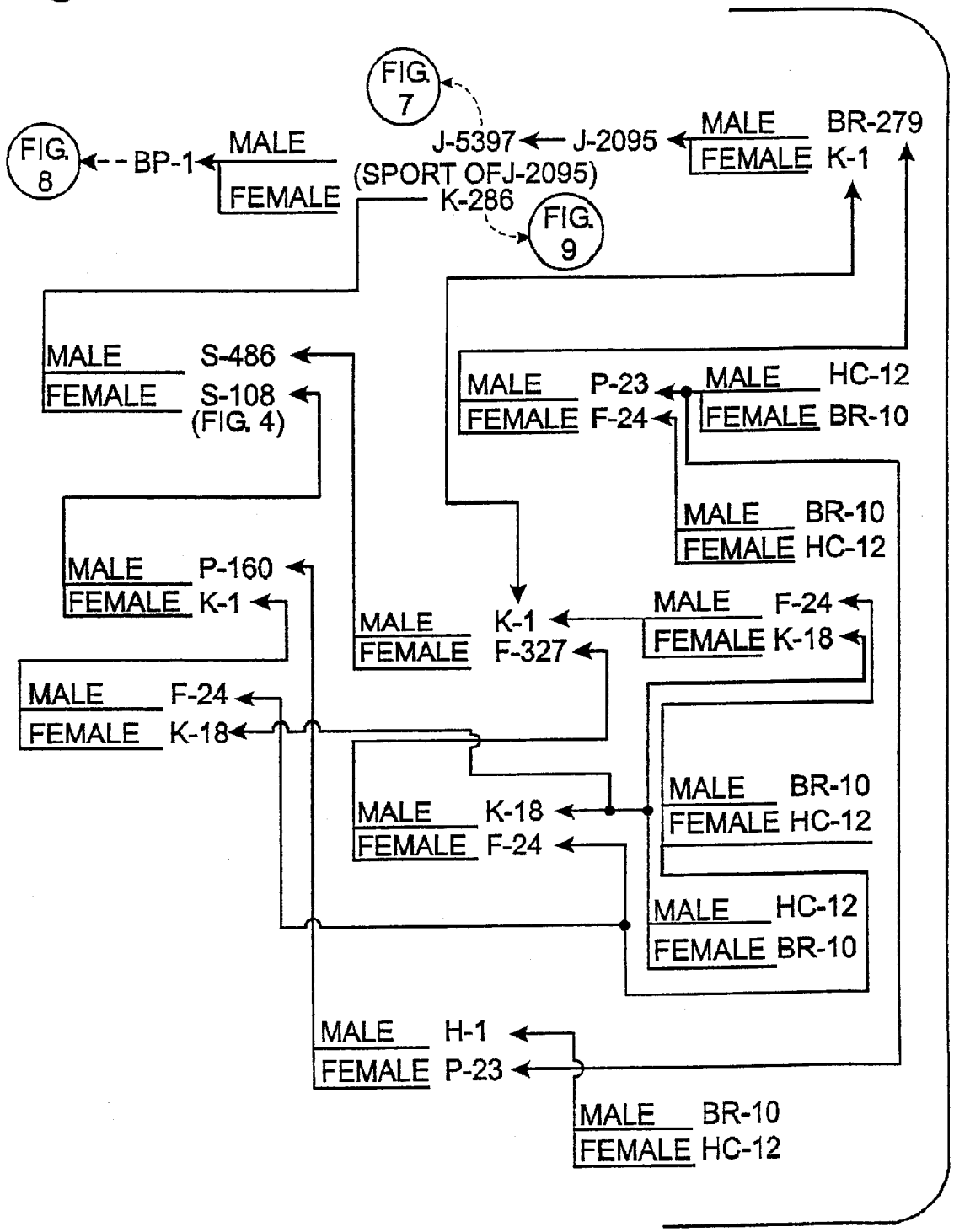
Figure 13:
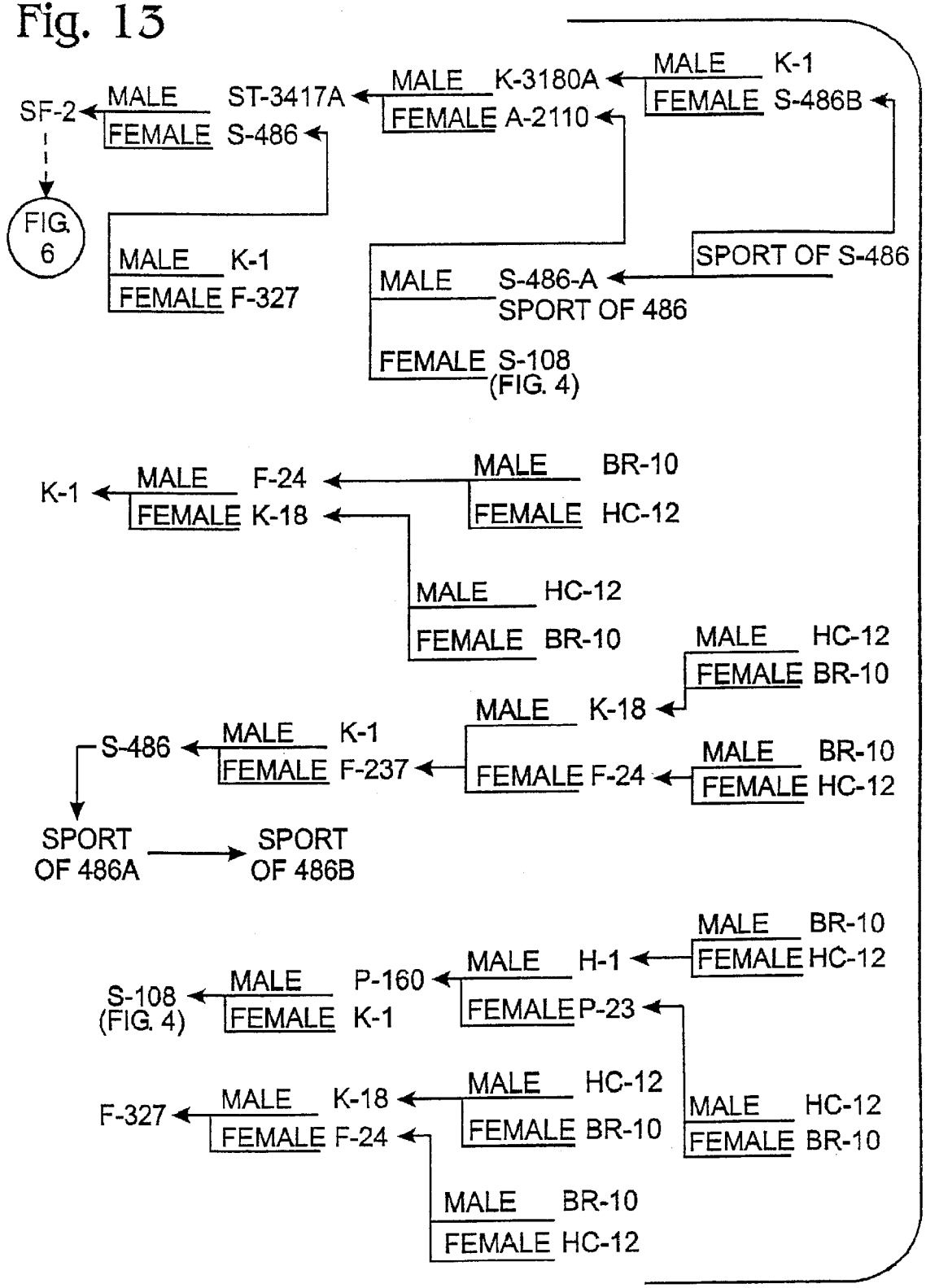

Looking now to FIGS. 11–13, the lineages of certain example plants of this invention are shown. In FIGS. 11–13, plant identification codes correspond to the same ones used in Table 2, and when the codes are the same they refer to the same plant listed in Table 2. Generally, FIGS. 11–13 show the male and female parent plants in certain successive crosses, progeny, and asexually propagated plants. Plants produced from sports are noted. FIGS. 11–13 show the lineages of the plants shown in FIGS. 2–4 and 6–9.

FIG. 11 shows various lineages, including the lineage of the marbled plants of FIGS. 2a–3. The specific plants shown in FIGS. 2–3 were third generation clones from L-146 each identified as L-146-3. As indicated in FIG. 11, the plant identified as S-108 is the plant with multiple sports shown in FIG. 4. The lineage of the plant with multiple pediceling shown in FIG. 8 is identified as BP-1, among the lineages of FIG. 12. The plant identified as J-5397 is a sport of the plant identified as J-2095. J-5397 is the plant shown in FIG. 7 that produced twin ovaries directly from a single peduncle. The plant identified as K-286, which was crossed with J-5397, is the plant with multiple pediceling shown in FIG. 9. The plant shown in FIG. 6 is identified in FIG. 12 as SF-2.

Example

New Guinea Impatiens Plant Named "ElRed"

The following elaborates on the botanical features of one embodiment of a novel plant of the present invention shown in FIGS. 2–3. That plant coded L-146-3 was bred according to the methods of the present invention and has been named "ElRed". Its lineage is shown in FIG. 11. Cuttings of asexually reproduced seedlings of the plant producing the flower of FIGS. 2–3 are commercially available from Tioga Genetics, Broadbent, Oreg.

The cultivar of FIGS. 2–3 was developed and selected in a controlled breeding program in a controlled environment in Coquille, Oregon by the inventor named herein. ElRed was selected as a single lateral branch of an unnamed parent, coded L-146. The new and distinct cultivar, ElRed, is also disclosed in a co-pending plant application, naming Harlan Cosner as the inventor, U.S. Pat. No. 11,851 (hereinafter the Cosner Plant Application). The disclosure of that application is hereby incorporated by reference for the plants and flowers disclosed. (it is noted that the original variety, name for the subject of the Cosner Plant Application, "Electra Tie-Dye", has been changed to ElRed.)

In accordance with 37 C.F.R. §§1.801–809, twenty-five hundred seeds for El Red were deposited with American Type Culture Collection ("ATCC"), 10801 University Boulevard, Manassas, Va. 20110-2209 on May 10, 2001 and accorded ATCC accession number PTA-3367.

Asexual reproduction of the novel cultivar shown in FIGS. 2–3, based on terminal cuttings taken at Coquille, Oreg. and grown out in a controlled environment there, has shown that the unique features of ElRed are stable and reproduced true to type in successive generations of asexual reproduction.

Relative to single or multi-color flowers of conventional New Guinea impatiens plants, such as the Star or Bright Eye varieties, which have distinct non-random patterns, the colors on flowers of FIGS. 2–3 are distributed in distinct irregular, randomly distributed patterns on each petal and flower. The patterns are defined by multiple, irregularly-shaped regions of color. Generally, each region consists of an elongate streak or patch of color typically radiating in a direction from the base of a petal to the edge of the petal. The irregularly shaped regions, while not necessarily exclusive of other colors, generally are dominated by a single color. The streaks or patches forming regions may vary in shape, length, width, and color intensity. They also vary in terms of their position relative to the base and edge of a petal. The present cultivar differs from its parent in that predominantly every flower displays a random multi-colored pattern on nearly every petal of nearly every flower. The parent plant produced flowers with petals that were extremely variable from solid different colors to the current random multi-colored patterns of the present invention.

Color references are according to the Royal Horticultural Society Colour Chart, except where general terms of ordinary dictionary significance are used.

They illustrate the new and distinctive marbling effect in the flowers of ElRed. The photographs show the marbling effect in the flowers, colors in the flowers, foliage of the plant, and habit of the plant as true as reasonably possible. Flower and foliage colors in the photographs may appear different from the actual colors due to variables such as light reflectance and photo-processing conditions. To the extent, there may be differences between the photographs and the Colour Chart descriptions in the text, the textual descriptions control.

The following description of the plant and flowers in the photographs is based on the environmental and cultural practices at Coquille Oreg. The photographs were taken during late summer/early fall. The following measurements, values, and comparisons describe plants grown under a double layer of polyethylene with controlled temperatures typically ranging from about 58° F. to about 85° F. Light levels ranged from about 3500 to 7000 ft. candles. The individual plants in the container of FIG. 3 were grown in six (6") Azalea containers in a soiless medium of the Peatlite type. Fertility of the medium was 20-10-20 western special plus, minor trace elements applied at 175 PPM of Nitrogen constant feed, no leach.

The plants of the present invention have not been grown under all conditions. If the plants of the present invention are grown under other conditions, it is possible that some phenotypical variations will result, as may occur with any plant.

Parentage:

A sport from a controlled cross between female parent coded S-108 and male parent coded S-486A, both of which are proprietary seedlings of the inventor produced in a controlled breeding program. The coded plants are shown in the lineages described in FIGS. 11–13, accompanying text, and elsewhere herein.

Propagation:

Type cutting: Lateral tips of plants were the cuttings used for asexual reproduction.

Time to initiate roots: Approximately 14 to 21 days with shorter time in summer and longer time in winter.

Rooting Habit: The rooting habit is characterized by numerous, fibrous, and well-branched roots.

Plant Description:

FIG. 3 illustrates the overall plant characteristics, which are described in more detail below:

Plant Form and Habit: Medium vigorous, mounded to wide, upright vase shaped; a free branching habit with numerous large flowers per plant; shiny, dark green foliage: flowers held above or beyond the foliage; a compact to medium compact growth habit.

Rooting Habit—Fibrous and branching. Mature plants are about 22 to 28 cm in height, and about 28 to 35 cm in width. Both of these measurements are a function of age, the above environmental and cultural practices, and can vary accordingly.

Branches: Habit is free branching. Branches are about 0.5 cm diameter in the internodes and about 1.0 cms at the nodes. The branch lengths and internode lengths vary with plant age, environment and cultural practices. Color is translucent in type measuring 146B-C in the internodes, with a reddish appearance at nodes measuring close to 178A.

Foliage Shape: Shape is oblong lanceolate; cuneate to attenuate base; acuminate apex; serrate margin. Size of largest is about 12 cm long; 4 cm wide.

Foliage Color shiny adaxial surface 147A; abaxial surface of 147B; abaxial surface venation, main vein 152A at base and 146A toward apex, lateral veins are barely distinguishable; abaxial surface venation main vein 148B at base, darkening to 148A toward apex, with laterals close to 146A on the mature foliage. Juvenile foliage adaxial surface is 147A; Abaxial surface is 147B; adaxial surface venation in main vein is 146C at base, becoming indistinguishable at apex, lateral veins are indistinguishable; abaxial surface main vein is 146B at base, darkening to 146A toward apex, lateral veins are closest to 146A.

Petioles: about 1.5 cm. Long on largest leaves, half round, about 3 mm wide on top, depth of about 2 mm. Color on top is close to 152A to B with occasional reddish markings close to 178A; bottom color is 146B.

Flower Description:

The following flower traits have been repeatedly observed and are determined to be the unique characteristics of ElRed, either singly or in combination with other plant characteristics.

Flowering Type and Habit: Flowers in which predominantly every petal has a marbling effect as defined in the text above, illustrations of which are shown in FIGS. 2–3. The photographs show flowers with multicolor marbling where the random multi-colored patterns are primarily comprised of shades of a reddish purple and salmony pink to salmony orange with none being either dominant or in a fixed position. Free flowering and continuous.

Natural flowering season: Year around in greenhouse.

Flowers Borne: beyond foliage, arising from leaf axils.

Flower and Bud Colors: Adaxial surface has random markings of 51A, 50A, 61B and 71B, with a darker mark at base of 60A. Abaxial surface of the top petal has the typical center ridge which is close to 187B. The remainder of this petal and the other 4 petals has random markings close to 61C, 63A, and 43C. Top of buds prior to opening are 187B, sepals are as described. Solid color petals or flowers may occur that match one of the above colors. In commercial production it is expected that generally about 15% or less of the flowers may have one of one or more petals of a substantially solid color matching one of the above colors. Less than about 10% of the branches may produce flowers that are not marbled as described, but may be substantially solid colors matching one of the above colors.

Quantity of Flowers: usually 4 to 8 per whorl, with normally 17 to 25 open per plant at a time.

Typical Flower and Bud Sizes: Flowers are about 7 cm. wide; 7 cm. high; 1.25 cm. deep. The top center petal is about 5 cm wide and 3 cm deep; reinform in shape with rounded to retuse apex and entire margin. Each side petal is about 3.5 cm. wide and 3.5 cm. long; shape is reverse cordate with a cuneate base, a retuse apex, and entire margin. Each lower petal is about 4 cm. wide and 3.5 cm. long; deltoid in shape with. a cuneate base, retuse apex, and entire margin. The side and lower petals are fused at the base. The above measurements refer to the larger flowers. The buds prior to opening are about 2.25 cm in length; about 1.5 cm in diameter; shape is ovoid.

Peduncles: About 5 cm. long; 2 mm. in diameter; colored on top close to 166B, bottom close to 145B, close to 141C where attached at axil.
  Spur About 7 cm. long, and 3 mm. in diameter at sepal end; shape is acicular, curved tube wider at sepal end. Color is 187C at sepal end with a greenish tip close to 145B.
  Sepals: 3; one attached to the spur measuring about 1.7 cm. wide, and 2 cm long; rounded oval in shape with a pointed apex; adaxial surface is marked randomly with 63B an d a lighter whitish-pink, difficult-to-rate color with 63A toward apex end; the abaxial surface is randomly marked close to 63B and 62B with a greenish tip close to 144B. Each other sepal is about 7 mm. wide and 1.8 cm. in length; both surfaces appear close in coloration with the adaxial surface being more translucent, markings are of 185B and 142C, with an elongated tip of 143A to B.
  Reproductive organs: Ovary is colored 143A; about 6 mm. in length; 2 mm in diameter, stigma is whitish green translucent; about 2 mm wide. The anther is a single fused organ wrapped around the ovary with 5 spur-like attachments at the base; colored 185A at the base, and 161D at the top. The Pollen color is closest to 4D. The pollen and anther are both shed prior to the stigma being receptive to the sperm nucleus of the pollen; natural seed production seldom occurs as a result.

Disease Resistance:
  Problems from fungal, bacterial, or viral pathogens have not been observed.

Figure 17:
FIG. 17 shows another example of a novel marbled New Guinea impatiens plant according to the present invention.

Seed Production:
  Self-sterile.
  Turning to FIG. 17, another example of a marbled New Guinea impatiens plant flower may be seen. This plant was coded as F-EL-1 under the inventor's breeding program. F-EL-1 was selected from a cross of L-146-3 (pollen parent) and S-286C (seed parent). S-286C was a clone selected from K-286 for its stable marbling characteristics. (Again, plant codes correspond to the plants in Table 2 above.)

F-EL-1 was generally similar to L-146-3 described in the example above. It was produced at the same location under a similar breeding program and under similar growth conditions. One respect that F-EL-1 differs from L-146-3 is in terms of color. F-EL-1 also shows good marbling characteristics like L-146-3, but is notably more pinkish in color. Further, marbled varieties having red-orange bicolor, and salmon-light coral bicolor are currently under development. The development of F-EL-1 helps demonstrate that the marbling trait is not dependent or linked to color. It also helps demonstrates that marbling is a stable trait.

Returning to the methods of breeding the novel plants of the present invention, it has been observed that certain novel pollen collection and transfer methods enhance the likelihood that marbling will be seen in the off-spring of a cross according to the methods taught herein.

FIGS. 18–20 illustrate certain reproductive structures of a typical New Guinea impatiens plant. In New Guinea impatiens varieties, each flower has an anther and an ovary. The anther is pronged and fits over the ovary. The flower sheds the anther as the plant matures. The anther sheds following shedding of the pollen. The features illustrated in the figures include a petal 110, an anther 112 with pollen 114 in pollen cavity 116. As illustrated in FIG. 19, anther 112 sits over immature ovary 124 (which is partially illustrated in phantom lines). FIG. 20 illustrates ovary 124 without anther 112. In FIG. 20, the anther has been shed and the ovary has matured, revealing stigma 126. The reproductive structures also include stigma 126 at the top of ovary 124.

Petal 110 includes an off-color region 118 that is indicative of the marbling trait, as previously described. This off-color region 118 may be in the form of a stripe and may extend into the anther 112. The off-color region 118 may be defined by boundaries or edges 119a and 119b where there is a generally visible transition from the off-coloring to a dominant color region 120a and 120b of the petal. Preferably, the off-coloring is found on a plant that otherwise appears conventional, such as a plant with a solid pattern, star pattern, or bright eye pattern.

In the method for enhanced marbling, pollen 114 is removed from lower off-color region 122a or 122b of off-color region 118 on anther 112, close to the boundaries 119a and 119b. Removal of pollen from a region 122a or 122b that is within about 1 mm of either side of a boundary 119a or 119b should produce an enhanced marbling effect. (However, the present invention is not intended to be limited to this measure, persons skilled in the art being appreciative of or capable of readily ascertaining other effective measures from the teachings herein.) If the off-color region 118 does not extend into anther 112, pollen 114 should be selected from a region that is near boundary 119a or 119b. Preferably, the region is as close to the stripped region as possible.

If the off-color region 118 extends into ovary 124, the pollen 114 should be applied to the stigma in a region 128a or 128b that is on or close to boundary 119a or 119b of off-color region 118. Preferably, pollen is placed directly on boundary 119a or 119b. If off-color region 118 does not extend into ovary 124, the pollen should be applied in accordance with the foregoing but relative to the region on stigma 126 to which off-color region 118 and boundaries 119a and 119b extrapolate.

In the foregoing method for enhanced breeding, the pollen collection and transfer techniques may be any that are known to persons skilled in the art. The present method teaches novel locations for collection and placement of pollen using the known techniques.

Persons skilled in the art will recognize the foregoing description and embodiments are not limitations but examples. It will be recognized by persons skilled in the arts that many modifications and variations to the present invention are possible that are still within the spirit and scope of the teachings and claims contained herein.

What is claimed:

1. A New Guinea impatiens plant having at least two flowerable pedicels arising from at least one peduncle on at least one branch of the plant, said plant being asexually reproducible into a plant having about the same degree of multiple pediceling, wherein the plant includes marbling in its background.

2. The plant of claim 1 wherein at least one peduncle has at least three pedicels.

3. The plant of claim 1 wherein at least one branch on the plant has at least two peduncles each giving rise to multiple pedicels.

4. The plant of claim 1 wherein at least two branches on the plant each have at least one peduncle giving rise to multiple pedicels.

5. A New Guinea impatiens plant having at least two flowerable pedicels arising from at least one peduncle on at least one branch of the plant, said plant being asexually reproducible into a plant having about the same degree of multiple pediceling, wherein the plant includes marbling in its genetic background.

6. The plant of claim 5 wherein two or more branches on the plant each have at least one peduncle giving rise to multiple pedicels.

7. The plant of claim 5 wherein the plant further includes two or more peduncles on a single branch, each giving rise to multiple peduncles.

8. A method of producing a New Guinea impatiens plant comprising:
(a) crossing a New Guinea impatiens plant having marbling in its genetic background with a different or same New Guinea impatiens plant;
(b) selecting progeny that show some degree of multiple pediceling in at least one or more peduncles on a branch; and
(c) repeating steps (a) to (b) as necessary until a plant is produced having at least two flowerable pedicels arising from at least one peduncle on at least one branch of the plant, said plant being asexually reproducible into a plant having about the same degree of multiple pediceling.

9. The method of claim 8 wherein steps (a) to (b) are repeated as necessary until the produced plant has at least one peduncle with at least three pedicels.

10. The method of claim 8 wherein steps (a) to (b) are repeated as necessary until the produced plant has at least one branch with at least two peduncles each giving rise to multiple pedicels.

11. The method of claim 8 wherein the steps are repeated as necessary until at least two branches on the plant each have at least one peduncle giving rise to multiple pedicels.

12. A method of producing a New Guinea impatiens plant comprising:
(a) crossing a New Guinea impatiens plant having multiple pediceling in its background with a different or same New Guinea impatiens plant having multiple pediceling in its background wherein at least one of the parents in the initial cross has marbling in its genetic background;
(b) selecting progeny that show some degree of multiple pediceling in at least one or more peduncles on a branch; and
(c) repeating steps (a) to (b) as necessary until a plant is produced having at least two flowerable pedicels arising from at least one peduncle on at least one branch of the plant, said plant being asexually reproducible into a plant having about the same degree of multiple pediceling.

13. The method of claim 8 wherein the plant selected in step (b) has a higher degree of multiple pediceling than either parent plant.

14. The method of claim 12 wherein during any initial or repeat cross of step (a), the initial plant or selected plant from step (b) produces about 30% or more of its flowers with a marbling effect.

15. The method of claim 8 further comprising a step wherein a selected plant is self-pollinated.

16. The method of claim 8 wherein a selected plant is crossed with other selected plants in one or more crosses of the method.

17. The method of claim 8 wherein a selected plant is backcrossed to one of its parents in one or more crosses of the method.

18. The method of claim 8 wherein the steps are repeated until about 30% or more of the branches in the produced plant each have at least one peduncle with multiple flowerable pedicels.

19. A New Guinea impatiens plant having at least two branches each with at least one peduncle, said plant having marbling in its genetic background, said plant being asexually reproducible into other plants showing at least two branches each having at least one peduncle with multiple pedicels.

20. The plant of claim 5 wherein said plant further includes at least two sports.

21. The plant of claim 20 wherein said plant includes at least two sports producing a conventional flower type.

22. The plant of claim 1 wherein the plant displays flowers predominantly all of which are of a conventional type.

23. The plant of claim 1 wherein the plant displays flowers predominantly all of which are of a marbled type.

24. A double New Guinea impatiens plant having marbling in its genetic background and having at least two branches each with at least one peduncle with multiple pedicels said plant being asexually reproducible into other plants with about the same degree of multiple pediceling.

25. A method of producing a New Guinea impatiens plant comprising:
selecting a first New Guinea impatiens plant having a predetermined degree of marbling, the first plant being asexually reproducible into other plants having a similar degree of marbling;
selecting a second predetermined New Guinea Impatiens plant;
crossing the first and second plants;
selecting progeny that show a desired characteristic; and
asexually propagating progeny showing the desired characteristic.

26. The method of claim 25 wherein the plant with multiple pedicels has at least two peduncles, each with multiple pedicels.

27. The method of claim 26 wherein the plant with multiple pedicels has at least three branches with at least one peduncle per branch producing multiple pedicels.

28. A method of producing a New Guinea impatiens plant comprising: selecting a first New Guinea impatiens having a predetermined degree of marbling and a flower having a petal with an off-colored region indicative of marbling, the off-colored region having at least one boundary, said off-colored region optionally extending into an anther or an ovary of said flower, collecting pollen from a region of an anther that is on or in close proximity to a boundary for use in pollinating a seed parent plant comprising the same or a different New Guinea plant having a predetermined degree of marbling; applying collected pollen onto an area of the stigma, the pollen being applied to the stigma of the seed parent plant on or closely adjacent a boundary of an off-color region indicative of marbling; and allowing the pollinated plant to produce a fertilized seed; and growing seed into a plant.

29. The method of claim 28 wherein the off-color region is generally in the form of a stripe and extends into an anther of the pollen parent.

30. The method of claim 28 wherein the off-color region is defined by boundaries or edges where there is a generally visible transition from the off-coloring to a dominant color region of the petal.

31. The method of claim 30 wherein the pollen is removed from lower off-color regions of the anther where the petal is integral with the anther, close to a boundary of the off-colored region.

32. The method of claim 28 wherein the off-color region extends into the ovary of the seed parent, and pollen is applied to the stigma in a region that is close to a boundary of the off-color region.

33. A New Guinea impatiens plant having marbling in its, genetic background, the plant providing at least 16 flowers per whorl, the plant also displaying multiple peduncles, a plurality of said peduncles each having multiple pedicels.

34. A New Guinea impatiens plant having multiple peduncles, a plurality of said peduncles each having multiple pedicels, the plant being capable of producing an inflorescence of at least 30 flowers open at a time.

35. A New Guinea impatiens plant according to claim 1 wherein the plant is directly or indirectly descended from the cultivar "El Red" having American Type Culture Collection accession number PTA-3367.

* * * * *